United States Patent

Arita

[11] Patent Number: 6,036,316
[45] Date of Patent: *Mar. 14, 2000

[54] VISUAL AXIS DETECTING DEVICE AND APPARATUS INCLUDING VISUAL AXIS DETECTING DEVICE

[75] Inventor: Hiroshi Arita, Kawasaki, Japan

[73] Assignee: Canon Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/941,378

[22] Filed: Sep. 30, 1997

[30] Foreign Application Priority Data

Oct. 2, 1996 [JP] Japan ................................. 8-279923
Oct. 2, 1996 [JP] Japan ................................. 8-279925

[51] Int. Cl.$^7$ ........................................................ A61B 3/14
[52] U.S. Cl. ........................... 351/210; 351/212; 351/205
[58] Field of Search .................................. 351/305, 306, 351/210, 211, 212, 247

[56] References Cited

U.S. PATENT DOCUMENTS

| | | | |
|---|---|---|---|
| 5,657,109 | 8/1997 | Konishi | 351/206 |
| 5,671,447 | 9/1997 | Tokunaga | 396/51 |
| 5,719,388 | 2/1998 | Tokunaga | 396/51 |

FOREIGN PATENT DOCUMENTS

| | | |
|---|---|---|
| 1-274736 | 11/1989 | Japan . |
| 4-347131 | 12/1992 | Japan . |
| 4-347132 | 12/1992 | Japan . |
| 6-148509 | 5/1994 | Japan . |

*Primary Examiner*—Huy Mai
*Attorney, Agent, or Firm*—Fitzpatrick, Cella, Harper & Scinto

[57] ABSTRACT

A visual axis detecting device includes an image sensor for imaging an eyeball image and a visual axis detector for detecting a Purkinje image from the eyeball image imaged by the image sensor as well as for extracting pupil edges from a plurality of pupil edge candidates contained in the eyeball image and detecting the visual axis of a user using the Purkinje image and the pupil edges. The visual axis detector defines a reference point from the position of the Purkinje image, determines the distances from the reference point to the plurality of pupil edge candidates, respectively, and extracts the pupil edges from the plurality of pupil edge candidates by statistically processing the distances. With this arrangement, the visual axis detecting device can correctly extract the pupil edges at a high speed.

38 Claims, 23 Drawing Sheets

PRIOR ART

PRIOR ART

PRIOR ART

PRIOR ART

PRIOR ART

PRIOR ART

VISUAL AXIS DETECTING DEVICE AND APPARATUS INCLUDING VISUAL AXIS DETECTING DEVICE

BACKGROUND OF THE INVENTION

1. Field of the Invention

This invention relates to a visual axis detecting device for detecting the visual axis of a user, and more specifically, to a visual axis detecting device for detecting the visual axis of a user by extracting a pupil edge as a boundary between an iris and a pupil.

2. Related Background Art

Conventionally, there have been proposed various types of visual axis detecting devices for detecting where a person looks. For example, the device in Japanese Unexamined Patent Publication No. 1-274736 projects parallel light beams to an eyeball of an observer from a light source and determines a visual axis by making use of an image reflected from a cornea, that is, a so-called cornea reflected image (Purkinje image) and the imaging position of a pupil. An example of this visual axis detecting device will be described with reference to FIG. 12 to FIG. 18.

FIG. 12 is a block diagram showing the main portion of the electrical arrangement of the visual axis detecting device. Numeral 1 denotes a sequence controller for controlling the sequence of a system as a whole, numerals 2 and 3 denote a pair of IREDs disposed in parallel with each other in the direction horizontal to an observer to illuminate an eyeball of the observer, numeral 4 denotes an IRED driver for driving the IREDs 2, 3, numeral 5 denotes an imaging device such as a CCD or the like for reading an eyeball image illuminated by the IREDs 2, 3, numeral 6 denotes an A/D converter for subjecting an image signal read by the imaging device 5 to A/D conversion so that it can be easily processed, numeral 7 denotes a push switch for starting and stopping the detection of a visual axis and numeral 8 denotes a battery for supplying electric power to the entire system.

FIG. 13 is a flowchart showing a series of operations executed by the visual axis detecting device as a first conventional example, FIG. 14 is a view showing an eyeball image projected to the imaging device when the observer approaches the visual axis detecting device and his eyeball is in contact with the device and FIG. 15 is a graph showing an output image of a line where Purkinje images exist on the imaging device 5.

In FIG. 13, the sequence controller 1 first turns on the IREDs 2, 3 toward the eyeball of the observer (step #1). Next, the sequence controller 1 reads an eyeball image at the same time through the imaging device 5 and converts the eyeball image into an image signal by digitalizing it through the A/D converter 6 and stores the image signal to an internal RAM (step #2). Then, the sequence controller 1 extracts a Purkinje image by processing the image signal (step #3).

The Purkinje image is extracted in such a manner that when the image signal has a level higher than a given level and a large inclination, it is regarded as the Purkinje image by making use of the fact that the Purkinje image is bright and has a steep output. For example, it is assumed that an eyeball image is as shown in FIG. 14. In the eyeball image, although the Purkinje images are shown by a and b, since Purkinje image conditions for detecting the Purkinje images are set such that a signal level is $L_1$ (see FIG. 15) or higher and an inclination is greater than a given level, the Purkinje images a and b satisfy the conditions on a horizontal line $y_1$ as shown in FIG. 15 and the positions of them can be determined as Ipa and Ipb by the calculation of the center of gravity of the portions exceeding $L_1$, and the like.

Next, the sequence controller 1 extracts a pupil edge as a boundary between an iris and a pupil by processing the image signal (step #4).

The pupil edge is extracted in such a manner that when the signal has a given level (which is denoted by $L_2$ as shown in FIG. 15) and an inclination which continues for a predetermined period of time or longer, the intersection point of the signal with the given level $L_2$ is regarded as the pupil edge by making use of the fact that a pupil portion is dark and an iris portion is brighter than the pupil portion.

For example, when the eyeball image is as shown in FIG. 14, proper pupil edges in the horizontal line $y_1$ are shown by $e_1$ and $e_6$ in FIG. 15. However, since the bottom portions of the Purkinje images a and b also satisfy the conditions of the pupil edge, $e_2$, $e_3$, $e_4$ and $e_5$ shown, for example, in FIG. 15 are also processed as the pupil edges regardless of whether they are actually the pupil edges. To avoid the above problem, false pupil edges ($e_2$, $e_3$, $e_4$ and $e_5$ in FIG. 15) located in a certain region in the vicinity of the Purkinje images are removed after the pupil edges are extracted as proposed in Japanese Unexamined Patent Publication No. 6-148509 (step #5).

When the pupil edges are extracted (step #4), they are classified into two groups depending upon the directions of inclination of them when they are viewed from a pupil center, that is, they are classified into left edges which have a negative inclination ($e_1$ in FIG. 15) and right edges which have a positive inclination ($e_6$ in FIG. 15).

Although the false pupil edges in the vicinity of the Purkinje images are removed at step #5, false pupil edges are also made by eyelashes and other various types of noises in addition to the above false pupil edges.

The black points in FIG. 14 show all the edges including false pupil edges which can be detected. To remove these false pupil edges, the range in which true pupil edges exist is designated based on Purkinje image position information and the edges located outside of the range are removed as proposed in Japanese Unexamined Patent Publication No. 4-347132 (step #6).

In FIG. 14, F shows the designated range and edges located outside of the range F, for example, the edges $e_{10}$, $e_{11}$ and the like are removed. Some false edges still remain even if the removing means is employed. To further remove the false edges, the sequence controller 1 statistically processes the remaining false edges and removes the edges which are greatly deviated from the overall edges, as false edges as proposed in Japanese Unexamined Patent Publication No. 6-148509 (step #7).

FIG. 16 is a subroutine showing the "removal by statistic".

In FIG. 16, determined first are the average $m_{LH}$ and the standard deviation $\sigma_{LH}$ of the horizontal coordinate of the left edge group (black points shown in FIG. 17) in the remaining edges (step #21). Then, the edges having the coordinates which are greatly deviated from the standard deviation in the left edges, that is, the edges having the coordinates represented by any one of the following formulas are removed (step #22):

horizontal coordinate>$m_{LH}+\sigma_{LH}$ horizontal coordinate<$m_{LH}-\sigma_{LH}$.

Next, the average $m_{LV}$ and the standard deviation $\sigma_{LV}$ in the vertical coordinate of the remaining left edge group are determined (step #23). Then, the edges having the coordinates which are greatly deviated from the standard deviation in the left edge group, that is, the edges having the coordinates represented by any one of the following formulas are removed (step #24).

vertical coordinate>$m_{LV}$+σ'LV vertical coordinate<$m_{LV}$−σ$_{LV}$

Likewise, the average $m_{RH}$ and the average deviation σ$_{RH}$ in the horizontal direction of the right edge group (step #25) are determined and the edges having the coordinates which are greatly deviated from the standard deviation in the right edge group, that is, the edges having the coordinates represented by any one of the following formulas are removed (step #26):

horizontal coordinate>$m_{RH}$+σ$_{RH}$ horizontal coordinate<$m_{RH}$−σ$_{RH}$.

Next, the average $m_{RV}$ and the standard deviation σ$_{RV}$ in the vertical direction of the remaining right edge group are determined (step #27). Then, the edges having the coordinates which are greatly deviated from the standard deviation in the right edge group, that is, the edges having the coordinates represented by any one of the following formulas are removed (step #29):

vertical coordinate>$m_{RV}$+σ$_{RV}$ vertical coordinate<$m_{RV}$−σ$_{RV}$.

On the completion of the above processing, a pupil center is detected at step #8 in FIG. 13. The pupil center is determined by the method of least squares or the like by making use of the fact that a pupil portion has a round shape (e.g., a circular shape or an oval shape). After the calculation of the pupil center, a pupil circle estimating error CER is calculated based on the position of the thus determined pupil center and the positions of the respective pupil edges in order to check the certainty of the calculated value (step #9). The calculation is executed using a square error as proposed in Japanese Unexamined Patent Publication No. 4-347131. Then, it is checked whether the determined pupil circle estimating error CER is equal to or less than a threshold value $C_T$ or not (step #10). When it is equal to or less than the threshold value $C_T$, the rotational angle of an eyeball is calculated based on the position of the determined pupil center and the positions of the Purkinje images (step #12) and the detection of the visual axis is finished.

Whereas, when the pupil circle estimating error CER is greater than the $C_T$ at step #10, since a lot of false pupil edges are contained in the edges, the false pupil edges are further removed, that is, a "correction of the pupil circle" is executed (step #11) and the process returns to the calculation of the pupil center again (step #8).

FIG. 18 is a flowchart explaining the "correction of the pupil circle" at step #11.

In FIG. 18, the sequence controller 1 first checks whether the pupil circle is corrected a first time (first correction) or not (step #31). When it is corrected a first time, the pupil circle estimating error CER is stored as CER$_0$ (step #33) and one edge is removed (step #35). An order according to which the edges are removed is not particularly taken into consideration here and it is assumed that the left edges are removed first for the time being and the edges in the left edge group are removed in the order they are stored in a memory in the sequence controller 1 (ordinarily, the order they are extracted).

When the correction of the pupil circle at step #301 is not the first time, that is, when the process returns to step #8 in FIG. 13 after the pupil circle is corrected a first time, a second time or thereafter and then executes the "correction of the pupil circle" again at step #11 because the pupil circle estimating error CER is not less than $C_T$ again at step #10, it is checked whether the thus determined latest pupil circle estimating error CER is made smaller than the pupil circle estimating error CER before the edge is removed, that is, smaller than CER$_0$ (this means that the removed edge is the false pupil edge and the pupil circle is made nearer to a true circle) or not (step #32). Unless "CER<CER$_0$" here, the removed edge is returned to the original position because it is not a false pupil edge (step #34) and a next edge is removed in the order the edges are arranged (step #35).

When "CER<CER$_0$" at step #32, the removed edge is left as it is and the pupil circle estimating error CER is stored as CER$_0$ (step #33) and a next edge is removed in the order the edges are arranged (step #35) and the process returns to step #8.

Next, a second conventional example will be described with reference to FIG. 19 to FIG. 21.

FIG. 19 is a flowchart showing a series of the operations executed by the visual axis detecting device as a second conventional example. Note, the electrical arrangement of the visual axis detecting device is the same as that shown in FIG. 12.

In FIG. 19, a sequence controller 1 turns on IREDs 2, 3 toward the eyeball of an observer (step #41). Next, the sequence controller 1 reads an eyeball image at the same time through an imaging device 5 and converts the eyeball image into an image signal by digitalizing it through an A/D converter 6 and stores the image signal to an internal RAM (step #42). Then, the sequence controller 1 extracts a Purkinje image by processing the image signal (step #43).

The Purkinje image is extracted in such a manner that when the image signal has a level higher than a given level and a large inclination, it is regarded as the Purkinje image by making use of the fact that the Purkinje image is bright and has a steep output. For example, it is assumed that an eyeball image is as shown in FIG. 14. In the eyeball image, although the Purkinje images are shown by a and b, since Purkinje image conditions for detecting the Purkinje images are set such that a signal level is $L_1$ (see FIG. 15) or higher and an inclination is greater than a given level, the Purkinje images a and b satisfy the conditions on a horizontal line $y_1$ and the positions of them can be determined as Ipa and Ipb by the calculation and the like of the center of gravity of the portions exceeding $L_1$.

Next, the sequence controller 1 extracts a pupil edge by processing the image signal (step #44).

The pupil edge is extracted in such a manner that when the signal has a given level (which is denoted by $L_2$ as shown in FIG. 15) and an inclination which continues for a predetermined period of time or longer, the intersection point of the signal with the given level $L_2$ is regarded as the pupil edge by making use of the fact that a pupil portion is dark and an iris portion is brighter than the pupil portion.

For example, when the eyeball image is as shown in FIG. 14, proper pupil edges in the line $y_1$ are shown by $e_1$ and $e_6$ in FIG. 15. However, since the bottom portions of the Purkinje images a and b also satisfy the condition of the pupil edge, $e_2$, $e_3$, $e_4$ and $e_5$ are processed as the pupil edges regardless of wether they are the pupil edges. To avoid the above problem, false pupil edges ($e_2$, $e_3$, $e_4$ and $e_5$ in FIG. 15) located in a certain region in the vicinity of the Purkinje images are removed after the pupil edges are extracted, as proposed in Japanese Unexamined Patent Publication No. 6-148509 (step #45).

False pupil edges are also made by eyelashes and other various types of noises in addition to the false pupil edges in the vicinity of the Purkinje image. The black points in FIG. 17 represent all the edges including the false pupil edges which can be detected as described above. To remove these false pupil edges, the sequence controller 1 limits the range where true pupil edges exist based on Purkinje image position information as proposed in Japanese Unexamined Patent Publication No. 4-347132 (step #46).

FIG. 20 is a subroutine showing a "setting of the designated pupil range".

In FIG. 20, the left coordinate of the coordinates of two Purkinje images is represented by ($IP_1$, $JP_1$), the right coordinate of them is represented by ($IP_2$, $JP_2$) and the designated pupil range is set as shown below:

$$IS_1 \leftarrow IP_1 - 20$$

$$IS_2 \leftarrow IP_2 + 20$$

$$JS_1 \leftarrow (JP_1 + JP_2)/2 - 40$$

$$JS_2 \leftarrow (JP_1 + JP_2)/2 + 20$$

where, $IS_1$ represents the left limit of the designated pupil range, $IS_2$ represents the right limit thereof, $JS_1$ represents the upper limit thereof, and $JS_2$ represents the lower limit thereof.

According to the above arrangement, the set range is formed to a rectangular shape on a screen and has a range F to images as shown in FIG. 14.

On the completion of the flowchart in FIG. 20, a "removal of pupil edges outside of the designated pupil range" is executed at step #47 in FIG. 19.

FIG. 21 is a subroutine showing the "removal of pupil edges outside of the designated pupil range".

In FIG. 21, the edges which satisfy "horizontal coordinate<$IS_1$" and "horizontal coordinate>$IS_2$" are removed from all the edges which have been extracted at step #44 in FIG. 19 and then subjected to the "removal of pupil edges in the vicinity of the Purkinje image" at step #45 (steps #71, #72). Thereafter, the edges which satisfy "vertical coordinate<$JS_1$" and "vertical coordinate>$JS_2$" are removed from the remaining edges (steps #73, #74).

On the completion of the above processing, a pupil center is detected at step #48 in FIG. 19. The pupil center is determined by the method of least squares or the like by making use of the fact that a pupil portion has a round shape (including an oval shape). After the calculation of the pupil center, a pupil circle estimating error CER is calculated based on the position of the thus determined pupil center and the positions of the respective pupil edges in order to check the certainty of the calculated value (step #50). The calculation is executed using a square error as proposed in Japanese Unexamined Patent Publication No. 4-347131. Then, it is checked whether the determined pupil circle estimating error CER is equal to or less than a threshold value $C_T$, which is the reference of the certainty, or not (step #51). When it is equal to or less than the threshold value $C_T$, the rotational angle of an eyeball is calculated based on the position of the determined pupil center and the position of the Purkinje images (step #52) and the detection of the visual axis is finished.

Whereas, when the pupil circle estimating error CER is greater than the $C_T$ at step #50, since a lot of false pupil edges are contained in the edges, the false pupil edges are further removed, that is, the "correction of the pupil circle" (for example, FIG. 18) is executed (step #51) and the process returns to the calculation of the pupil center again (step #48).

A third conventional example will be described with reference to FIG. 24 to FIG. 29.

FIG. 24 is a flowchart showing a series of operations executed by the visual axis detecting device as the third example, FIG. 25 is a view of an eyeball image projected to the imaging device 5 in FIG. 12 when an observer approaches the visual axis detecting device and his eyeball is in contact with the device and FIG. 26 is a graph showing an output image of a line where Purkinje images exist on the imaging device 5.

In FIG. 24, a sequence controller 1 first turns on IREDs 2, 3 toward the eyeball of the observer (step #A1). Next, the sequence controller 1 reads an eyeball image at the same time through the imaging device 5 and converts the eyeball image into an image signal by digitalizing it through an A/D converter 6 and stores the image signal to an internal RAM (step #A2). Then, the sequence controller 1 extracts a Purkinje image by processing the image signal (step #A3).

The Purkinje image is extracted in such a manner that when the image signal has a level higher than a given level and a large inclination, it is regarded as the Purkinje image by making use of the fact that the Purkinje image is bright and has a steep output. For example, it is assumed that an eyeball image is as shown in FIG. 25. In the eyeball image, although the Purkinje images are shown by a and b, since Purkinje image conditions for detecting the Purkinje images are set such that a signal level is $T_P$ or higher and an inclination is greater than a given level, the Purkinje images a and b satisfy the conditions on a horizontal line y as shown in FIG. 26 and the positions of them can be determined as Xa and Xb by the calculation of the center of gravity of the portions exceeding $T_P$, and the like.

Next, the sequence controller 1 extracts a pupil edge by processing the image signal (step #A4).

The pupil edge is extracted in such a manner that when the signal has a given level (which is denoted by $T_D$ as shown in FIG. 26) and an inclination which continues for a predetermined period of time or longer, the intersection point of the signal with the given level $T_D$ is regarded as the pupil edge by making use of the fact that a pupil portion (portion c in FIG. 25) is dark and an iris portion (portion d in FIG. 25) is brighter than the pupil portion.

For example, when the eyeball image is as shown in FIG. 25, proper pupil edges in a horizontal line y are shown by $e_1$ and $e_6$ in FIG. 26. However, since the bottom portions of the Purkinje images a and b also satisfy the condition of the pupil edge, $e_2$, $e_3$, $e_4$ and $e_5$ are also processed as the pupil edges regardless of whether they are the pupil edges. Therefore, when a pupil center is determined by the method of least squares or the like using all the pupil edges, the pupil center is displaced by the false pupil edges and, as a result, the rotational angle of the eyeball of an observer which is determined finally is displaced.

Therefore, the sequence controller 1 previously removes the edges which are regarded as the false pupil edges within a certain region in the vicinity of the Purkinje image after the removal of the pupil edges in order to remove the false pupil edges at the bottom portion of the Purkinje image as proposed in Japanese Unexamined Patent Publication No. 6-148509 (step #A5).

An example of the processing at step #A5, that is, a processing for removing the false pupil edges within the certain region in the vicinity of the Purkinje image will be described with reference to the flowchart in FIG. 27.

When the coordinates of two Purkinje images a and b which have been extracted are represented by (Xa, Yb) and (Xb, Yb), respectively, the sequence controller 1 sets the width of a pupil edge removing region to k (tentatively, k=2) to both the coordinates in both the X-direction (horizontal direction) and the Y-direction (vertical direction), respectively (step #A501). Next, as the removal of the bottom portion of the Purkinje image a, the sequence controller 1 removes the edges in the respective regions equal to or greater than (XA−k) and equal to or less than (Xa+k) in the horizontal direction and equal to or greater than (Ya−k) and equal to or less than (Ya+k) in the vertical direction (step #A502). With this processing, the false pupil edges $e_2$ and $e_3$ shown in FIG. 26 are removed.

Next, the sequence controller 1 removes the false pupil edges within the respective regions equal to or greater than (Xb−k) and equal to or less than (Xb+k) in the horizontal direction and equal to or greater than (Yb−k) and equal to or less than (Yb+k) in the vertical direction as the removal of the bottom portion of the Purkinje image b (step #A503). With this processing, the false pupil edges $e_4$ and $e_5$ shown in FIG. 26 are removed.

Returning to FIG. 24, next, the sequence controller 1 determines the pupil center by the method of least squares or the like (step #A6) and the rotational angles of eyeballs $\theta_x$, $\theta_y$ by the pupil center and the Purkinje images a, b (step #A7), finally decides whether the derived values are correct or not (step #8) and finishes the detection of the visual axis.

SUMMARY OF THE INVENTION

According to one aspect of this invention, a visual axis detecting device for detecting a Purkinje image from an eyeball image imaged by an image sensor as well as extracting pupil edges from a plurality of pupil edge candidates contained in said eyeball image and detecting the visual axis of a user using said Purkinje image and said pupil edges is arranged such that a reference point is defined from the position of said Purkinje image, the distances from said reference point to said plurality of pupil edge candidates are determined, respectively, and said pupil edges are extracted from said plurality of pupil edge candidates by statistically processing said distances, whereby a pupil edge extracting operation can be correctly executed at a high speed.

According to the other aspect of this invention, a visual axis detecting device for detecting a Purkinje image from an eyeball image imaged by an image sensor as well as extracting pupil edges from a plurality of pupil edge candidates contained in said eyeball image and detecting the visual axis of a user using said Purkinje image and said pupil edges is arranged such that a predetermined region is set in the vicinity of said Purkinje images and the pupil edge candidates located in said predetermined region are removed when said pupil edges are extracted as well as the size of said predetermined region is changed in accordance with the interval between said plurality of Purkinje images, whereby a pupil edge extracting operation can be correctly executed.

DESCRIPTION OF THE PREFERRED EMBODIMENT

Embodiments of this invention will be described below with reference to the drawings.

Figure 1:
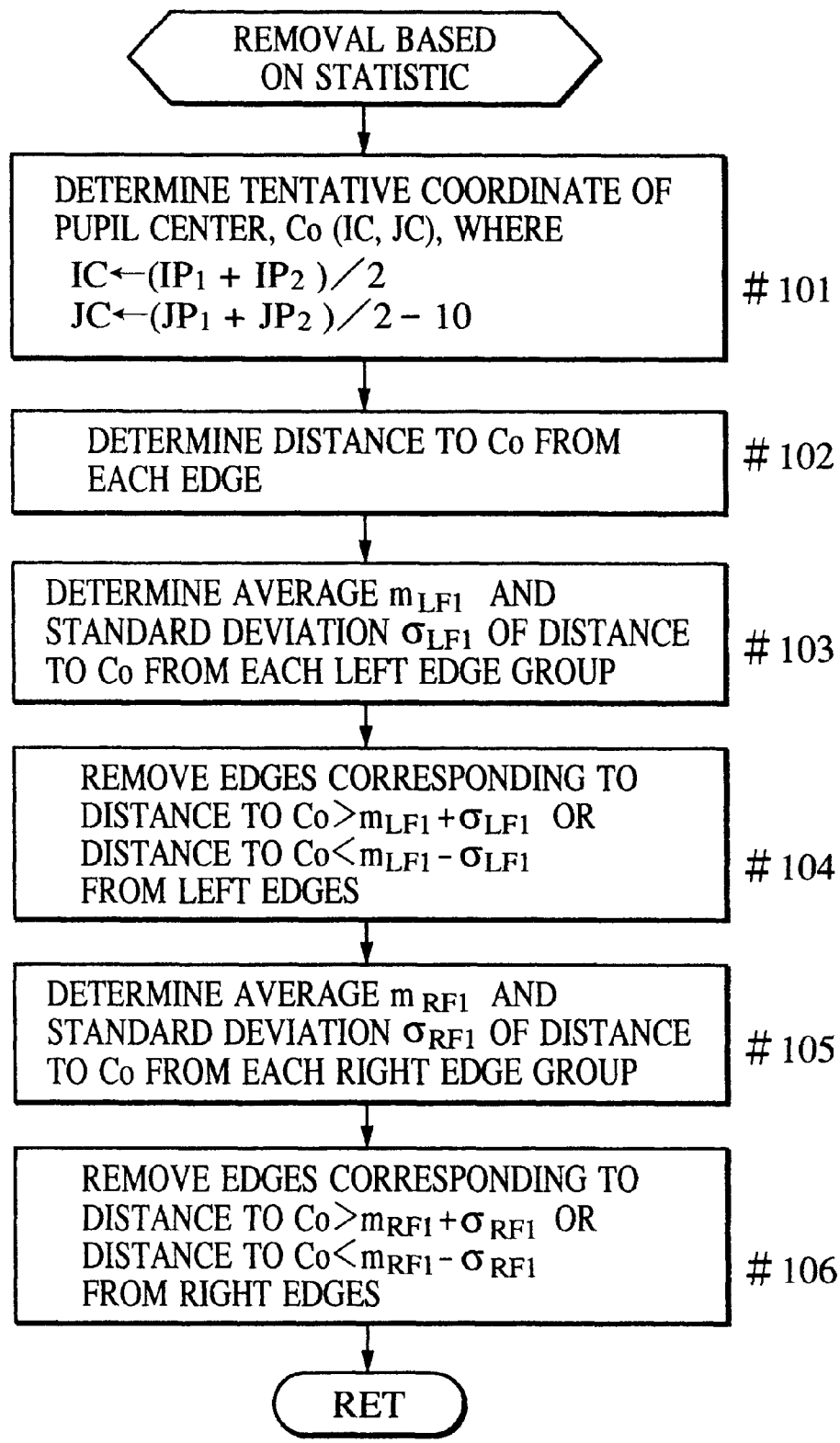
FIG. 1 is a flowchart showing the false pupil edges removing operation executed based on a statistic by a visual axis detecting device according to a first embodiment of this invention.
Figure 2:
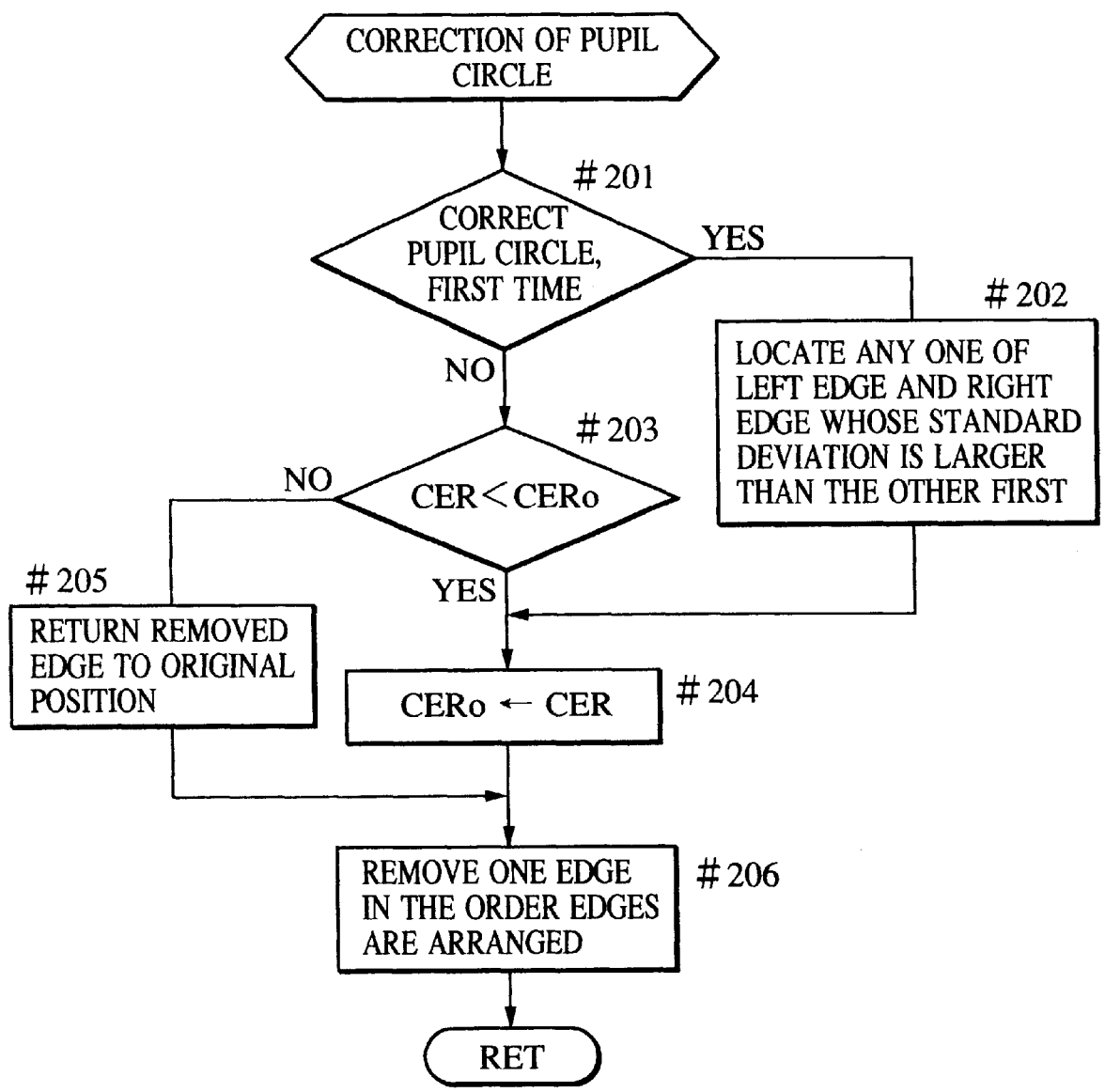
FIG. 2 is a flowchart showing a pupil circle correcting operation executed by the visual axis detecting device according to a second embodiment of this invention.
Figure 12:
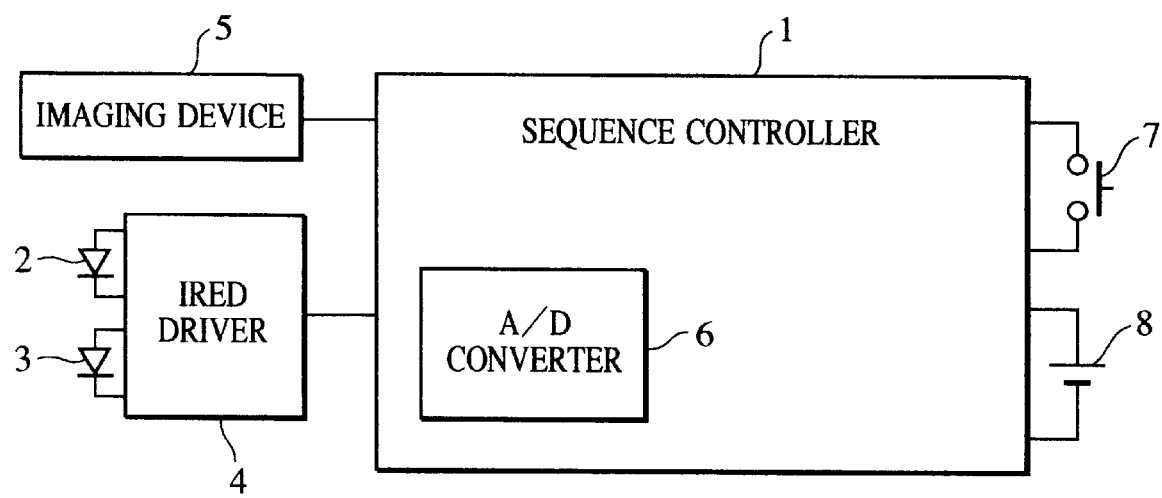
FIG. 12 is a block diagram showing the main portion of the electrical arrangement of the visual axis detecting device of this invention and a conventional visual axis detecting device.

FIG. 1 and FIG. 2 are flowcharts showing the operation of the main portion of a visual axis detecting device according to a first embodiment of this invention. Since the electrical arrangement of the visual axis detecting device is the same as that described in FIG. 12 and a series of operations of the visual axis detecting device is the same as that described in FIG. 13 except the processing of the "removal by the statistic" at step #7 and the processing of the "correction of the pupil circle" at step #11 in FIG. 13, the detailed description of the operation is omitted here.

First, the operation of the "removal by the statistic" will be described with reference to the flowchart shown in FIG. 1.

Since a pupil is formed in a circular shape, true pupil edges must be scattered so as to draw a circle, and thus the removal of the pupil edges based on the statistic must be executed based on the circle. Therefore, the position of the pupil center is tentatively estimated based on the detected position of a Purkinje image and the statistic is calculated based on the distances of respective edges from the pupil center.

In FIG. 1, a sequence controller 1 first determines a tentative pupil center position $C_0$ based on the positions of the Purkinje images. The left coordinate of the coordinates of the two Purkinje images is represented by ($IP_1$, $JP_1$), the right coordinate of them is represented by ($IP_2$, $JP_2$) and the coordinate (IC, JC) of the tentative pupil center position $C_0$ is determined as shown below (step #101):

$$IC \leftarrow (IP_1 + IP_2)/2$$

$$JC \leftarrow (JP_1 + JP_2)/2 - 10.$$

Next, the distances of respective edges to the tentative pupil center position $C_0$ are determined (step #102). When it is assumed, for example, that the coordinate of an edge is represented by ($IE_1$, $JE_1$), a distance $EC_1$ to be determined is represented by the following formula (1):

$$EC_1 = \sqrt{[(IC-IE_1)^2 + (JC-JE_1)^2]} \tag{1}$$

Next, the average $m_{LF1}$ and the standard deviation $\sigma_{LF1}$ of the distances to the pupil center position $C_0$ in the left edge group are determined from the thus obtained distance information (step #103). Then, the edges corresponding to the following formulas in the left edge group are removed (step #104):

distance to $C_0 > m_{LF1} + \sigma_{LF1}$ distance to $C_0 < m_{LF1} - \sigma_{LF1}$ Next, the average $m_{RF1}$ and the standard deviation $\sigma_{RF1}$ of the distances to the pupil center position $C_0$ in the right edge group are determined (step #105). Then, the edges corresponding to the following formulas in the right edge group are removed (step #106):

distance to $C_0 > m_{RF1} + \sigma_{RF1}$ distance to $C_0 < m_{RF1} - \sigma_{RF1}$.

Figure 3:
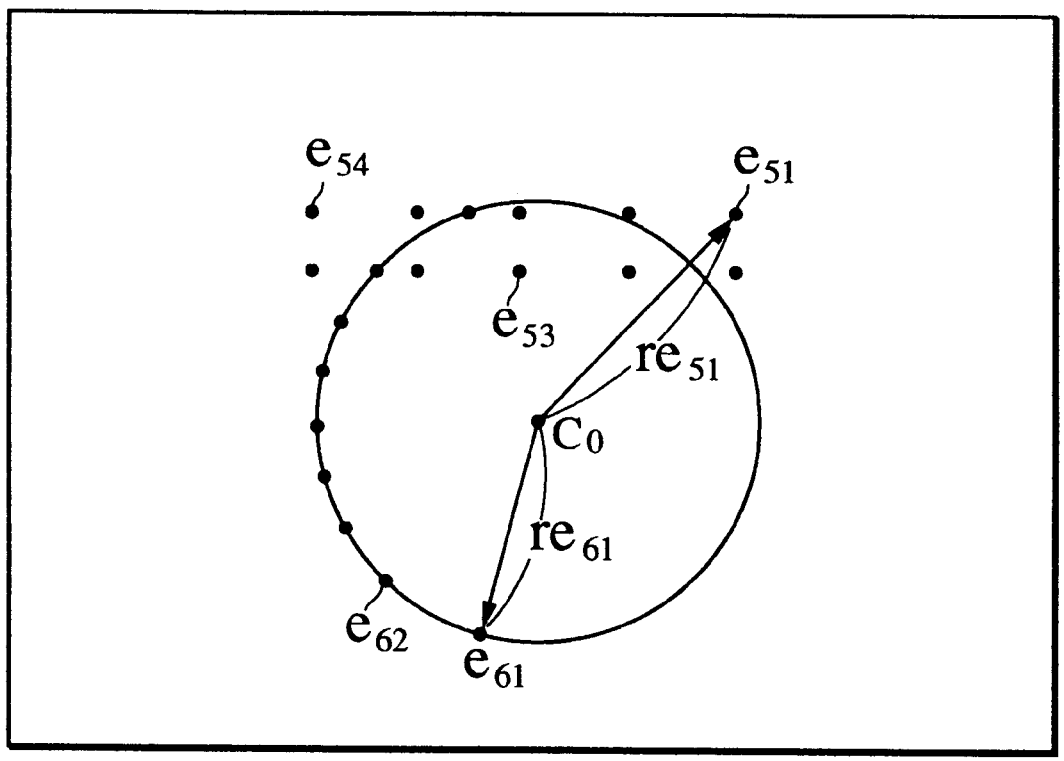
FIG. 3 is a view showing a pupil circle and a plurality of edges for supporting the operation in FIG. 2.

With the above processing, the edges can be removed based on the circle. For example, when it is assumed that the extracted left edges exist as shown by the black points in FIG. 3 (which are the same as the black points in FIG. 14) and the tentative pupil center position $C_0$ which is determined from the Purkinje images is located at the center of a circle having a radius $re_{61}$ as shown in FIG. 3, a false pupil edge $e_{51}$ is removed by the calculation of the statistic, likewise in the conventional example, and true pupil edges $e_{61}$ and $e_{62}$ are left without being removed in this embodiment, although they are removed in the conventional example.

As described above, a lot of true pupil edges can be left by the embodiment as compared with the conventional method.

Figure 13:
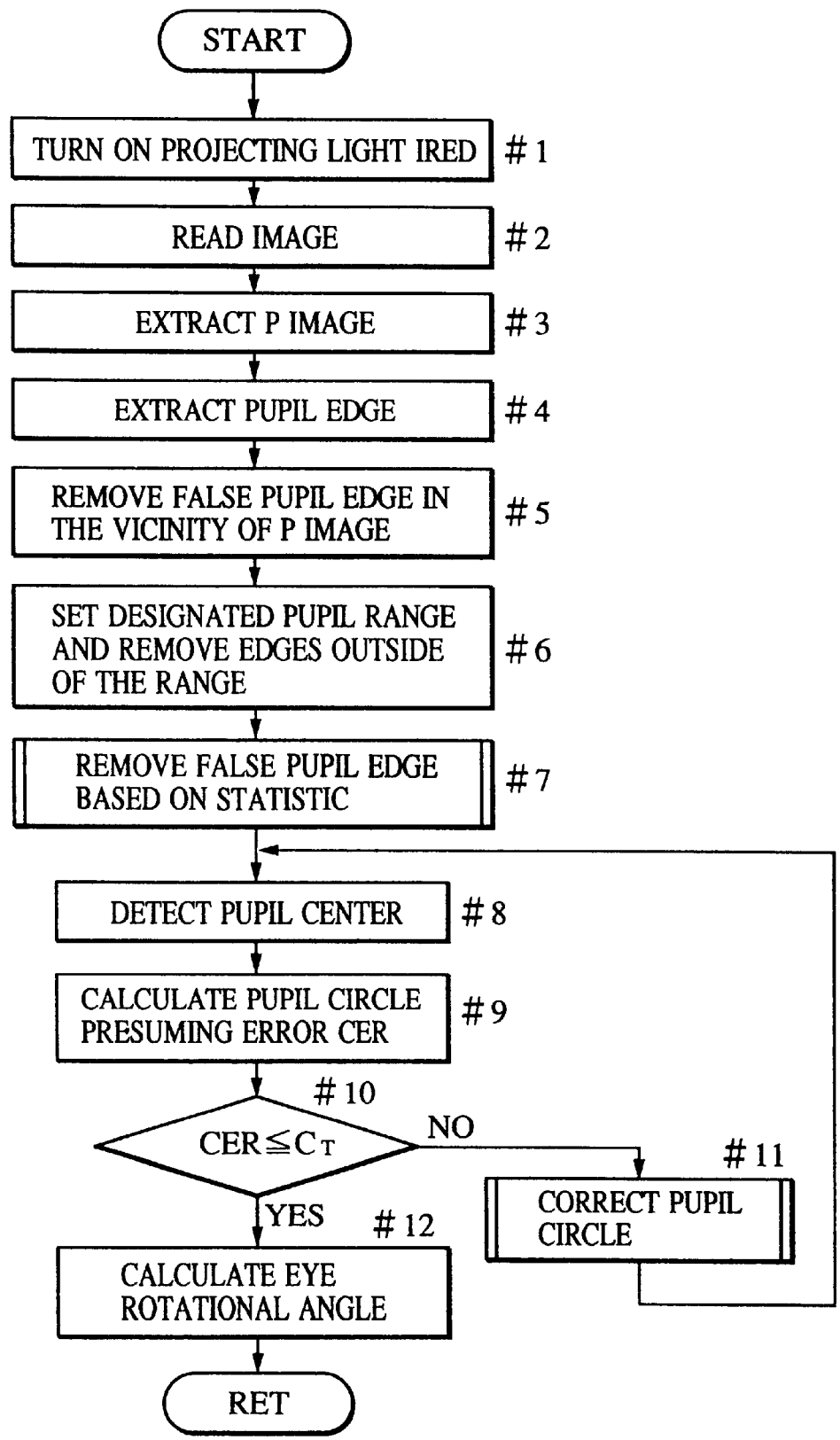
FIG. 13 is a flowchart showing a series of the operation executed by the visual axis detecting device shown in FIG. 12.

When the edge group which has a large standard deviation determined by the calculation of the above statistic is assumed to contain many false pupil edges in the right edge group and the left edge group and the edges in the above edge group are previously removed at step #11 in FIG. 13 following the above process, the circle can be effectively corrected.

The "correction of the pupil" will be described with reference to the flowchart in FIG. 2.

In FIG. 2, the sequence controller 1 first checks whether the correction of the circle is executed a first time (initial correction) or not (step #201). When it is corrected a first time, the standard deviations $\sigma_{LF1}$, $\sigma_{RF1}$ of the left edge group and the right edge group determined at steps #103, #105 are compared with each other and the order in which the left and right edge groups are arranged is changed so that the edges of the edge group including a larger standard deviation are removed first (step #202). Thereafter, a pupil circle estimating error CER is stored as $CER_0$ (step #204) and one edge is removed in the order the edges are arranged (step #206). Since the removal of the edge is executed a first time here, the above removed edge is the edge located at the leading side of the edge group having the larger standard deviation.

When the correction of the pupil circle at step #201 is not the first time, that is, when the process returns to step #8 in FIG. 13 after the pupil circle is corrected a first time, a second time or thereafter and then executes the "correction of the pupil circle" again at step #11 because the pupil circle estimating error CER is not less than $C_T$ again at step #10, it is checked whether the thus determined latest pupil circle estimating error CER is made smaller than the pupil circle estimating error CER before the edge is removed, that is, smaller than $CER_0$ (this means that the removed edge is the false pupil edge and the pupil circle is made nearer to a true circle) or not (step #203). Unless "CER<CER$_0$" here, the removed edge is returned to the original position because it is not a false pupil edge (step #205) and a next edge is removed in the order the edges are arranged (step #206).

When "CER<CER$_0$" at step #203, the removed edge is left as it is and the pupil circle estimating error CER is stored as CER$_0$ (step #204) and a next edge is removed in the order the edges are arranged (step #206).

Note, although the standard deviations are compared with each other in the state that the false pupil edges which are to be removed by the statistic are contained, the standard deviations may be calculated again with respect to the remaining edges after the execution of the "removal by the statistic" and the values of the standard deviations may be compared with each other.

(Second Embodiment)

Although the distances from the tentative pupil center C$_0$ (IC, JC) are calculated by determining the root as shown in the formula, the calculation of the root takes time.

On the other hand, if the symbol of the distance information is positive, the relative size of the distance also can be represented by the square of a distance, likewise. Therefore, when the average and the standard deviation are calculated from the squares of the distances without determining the root, the entire calculation time can be shortened as well as the same effect as that of the first embodiment can be obtained. This arrangement will be described below as a second embodiment.

Figure 4:
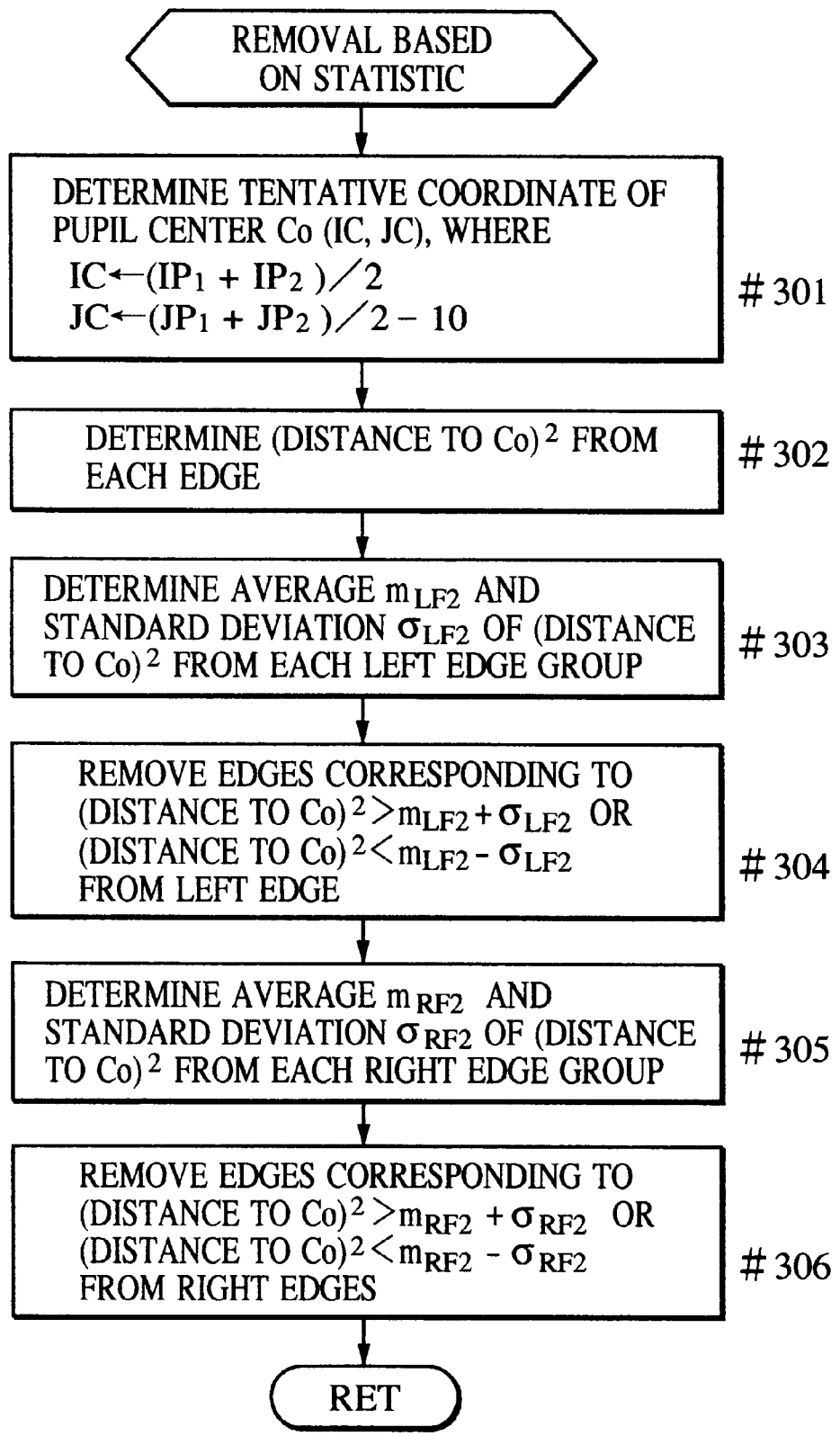
FIG. 4 is a flowchart showing a false pupil edge removing operation executed on a statistic by the visual axis detecting device according to the second embodiment of this invention.

FIG. 4 is a flowchart showing the operation of the main portion of the visual axis detecting device according to the second embodiment of this invention. Since the electrical arrangement of the visual axis detecting device is the same as that shown in FIG. 12 and a series of operations of the visual axis detecting device is the same as that shown in FIG. 13 except the processing of the "removal based on the statistic" at step #7 in FIG. 13, the detailed description thereof is omitted here.

In FIG. 4, a sequence controller 1 first determines a tentative pupil center position C$_0$ based on the positions of Purkinje images. The left coordinate of the coordinates of the two Purkinje images is represented by (IP$_1$, JP$_1$), the right coordinate of them is represented by (IP$_2$, JP$_2$) and the coordinate (IC, JC) of the tentative pupil center position C$_0$ is determined as shown below (step #301):

$$IC \leftarrow (IP_1 + IP_2)/2$$

$$JC \leftarrow (JP_1 + JP_2)/2 - 10.$$

Next, the squares of the distances to the pupil center position C$_0$ are determined as to respective edges (step #302). The calculation is carried out as follows. When a certain edge has a coordinate (IE$_1$, JE$_1$), the value EC$_1'$ to be determined is given by the following formula (2):

$$EC_1' = (IC - IE_1)^2 + (JC - JE_1)^2 \qquad (2)$$

Next, the average m$_{LF2}$ and the standard deviation σ$_{LF2}$ are determined from the (distance to pupil center position C$_0$)$^2$ of a left edge group in the thus determined squares of the distances to pupil center position C$_0$ (step #303). Then, the edges corresponding to the following formulas in the left edge group are removed therefrom (step #304):

(distance to C$_0$)$^2$ > m$_{LF2}$ + σ$_{LF2}$ (distance to C$_0$)$^2$ < m$_{LF2}$ − σ$_{LF2}$ Next, the average m$_{RF2}$ and the standard deviation σ$_{RF2}$ are determined from the squares of the distances to pupil center position C$_0$ of a right edge group (step #305). Then, the edges corresponding to the following formulas in the right edge group are removed therefrom (step #306):

(distance to C$_0$)$^2$ > m$_{RF2}$ + σ$_{RF2}$ (distance to C$_0$)$^2$ < m$_{RF2}$ − σ$_{RF2}$ (Third Embodiment)

Although the "removal based on the statistic" is executed independently as to the left edge group and the right edge group in the first and second embodiments, there is also contemplated a method of executing it to the entire edges. This arrangement will be described below as a third embodiment.

Figure 5:
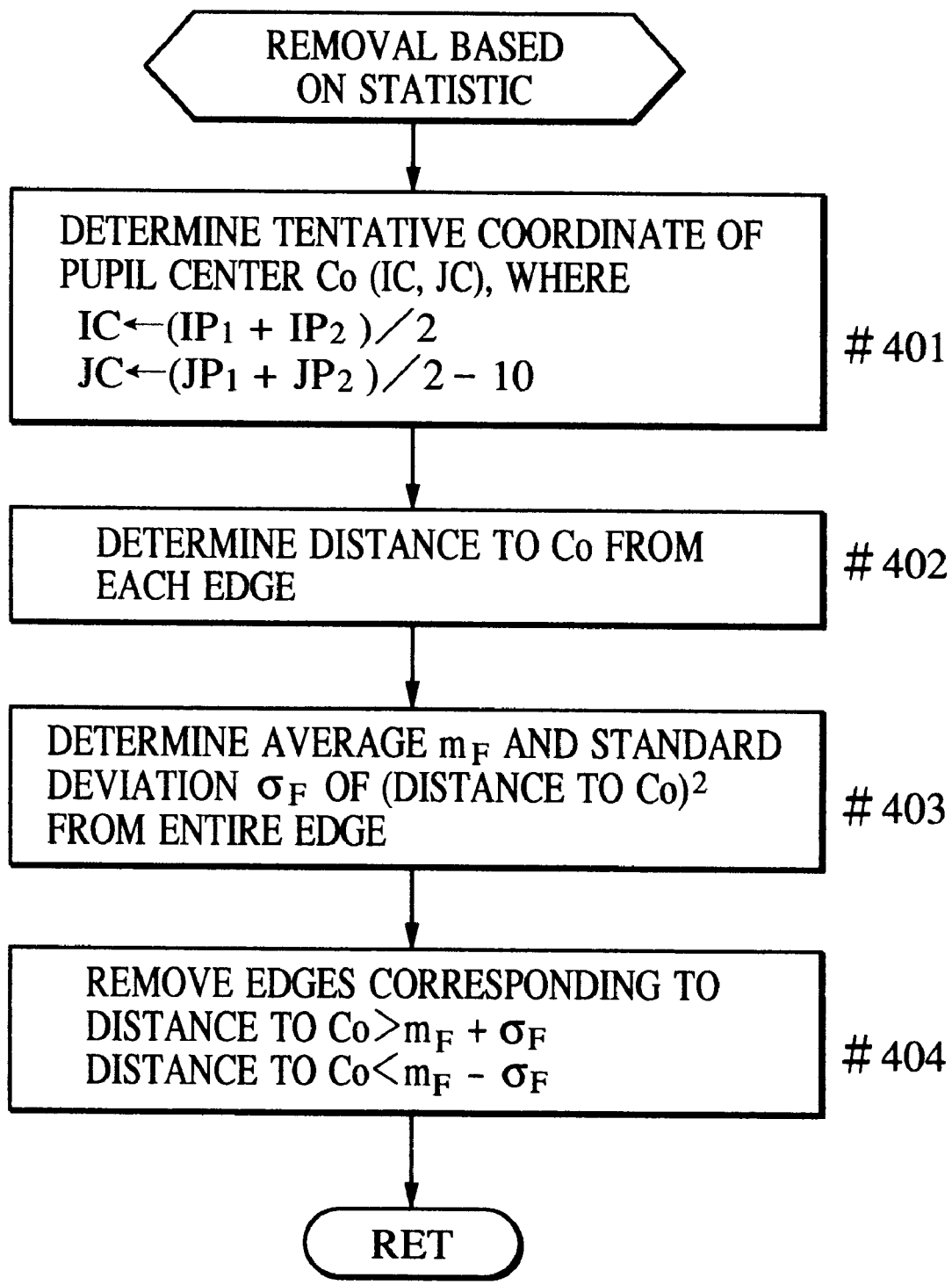
FIG. 5 is a flowchart showing a false pupil edge removing operation executed based on a statistic by the visual axis detecting device according to a third embodiment of this invention.

FIG. 5 is a flowchart showing the operation of the main portion of the visual axis detecting device according to the third embodiment of this invention. Since the electrical arrangement of the visual axis detecting device is the same as that shown in FIG. 12 and a series of operations of the visual axis detecting device is the same as that shown in FIG. 13 except the processing of the "removal based on the statistic" at step #7 in FIG. 13, the detailed description thereof is omitted here.

In FIG. 5, a sequence controller 1 first determines a tentative pupil center position C$_0$ based on the positions of Purkinje images. The left coordinate of the coordinates of the two Purkinje images is represented by (IP$_1$, JP$_1$), the right coordinate of them is represented by (IP$_2$, JP$_2$) and the coordinate (IC, JC) of the tentative pupil center position C$_0$ is determined as shown below (step #401):

$$IC \leftarrow (IP_1 + IP_2)/2$$

$$JC \leftarrow (JP_1 + JP_2)/2 - 10.$$

Next, the distance from each of the edges to the pupil center position C$_0$ is determined (step #402). This is determined by the same method as in the first embodiment. Next, the average mF and the standard deviation σ$_F$ of the distances of the entire edges to the pupil center position C$_0$ are determined (step #403). Then, the edges corresponding to the following formula are removed (step #404):

distance to C$_0$ > m$_F$ − σ$_F$.

distance to C$_0$ < m$_F$ − σ$_F$

According to the first to third embodiments, since the tentative pupil center position C$_0$ is set based on the position of the detected Purkinje imagges, the distance information from the center position C$_0$ to the respective edges is obtained and the false pupil edges are removed by executing the statistical processing to the thus obtained distance information, the false pupil edges are removed on the premise that true pupil edges exist on a circle (or an oval shape). Thus, a possibility that the removed edges are only false edges is increased, by which the edges can be effectively removed as compared with the conventional apparatus.

Further, in the correction of the pupil circle after the calculation of the pupil center, since the right and left edge groups having a large standard deviation which is determined by the calculation of the above statistic is assumed to contain many false pupil edges and the left edge group and they are previously removed, the pupil circle can be more effectively corrected, the calculation time can be shortened and the success ratio for detecting a visual axis can be increased.

Note, although the plurality of edges are divided into the right edge group and the left edge group in the above respective embodiments, they may be divided into a plurality of groups such as an edge group located far from the tentative pupil center position $C_0$ and an edge group located near to it, an upper edge group and a lower edge group or a right half edge group and a left half edge group on an imaging device.

(Fourth Embodiment)

Figure 6:
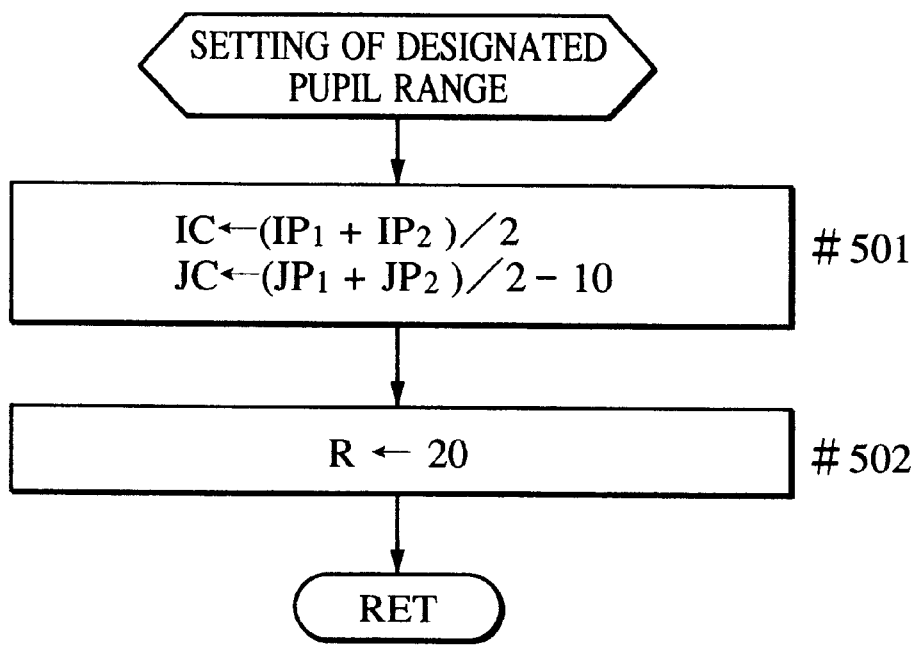
FIG. 6 is a flowchart showing a designated pupil range setting operation executed by the visual axis detecting device according to a fourth embodiment of this invention.

FIG. 6 is a flowchart showing the operation of the main portion of the visual axis detecting device according to a fourth embodiment of this invention. Since the electrical arrangement of the visual axis detecting device is the same as that shown in FIG. 12 and a series of operations of the visual axis detecting device is the same as that shown in FIG. 19 except the processing of the "setting of the designated pupil range" at step #46, the "removal of the pupil edges outside of the designated pupil range" at step #47 and the "correction of the pupil circle" at step #51 in FIG. 19, respectively, the detailed description thereof is omitted here.

In FIG. 6, a sequence controller 1 first determines a tentative pupil center position $C_0$ based on the positions of Purkinje images. The left coordinate of the coordinates of the two Purkinje images is represented by $(IP_1, JP_1)$ and the right coordinate of them is represented by $(IP_2, JP_2)$ and the coordinate (IC, JC) of the tentative pupil center position $C_0$ is determined as shown below (step #501):

$$IC \leftarrow (IP_1 + IP_2)/2$$

$$JC \leftarrow (JP_1 + JP_2)/2 - 10.$$

Next, the radius R of a circle having a center located at the tentative pupil center position is set to 20 so that the range of the circle coincides with a designated pupil range (step #502).

Although the radius R is set to the fixed value, it may be determined from a calculation formula based on an image magnification determined from the interval of the Purkinje images. After the determination of the radius R, the process returns to step #47 in FIG. 19.

Figure 7:
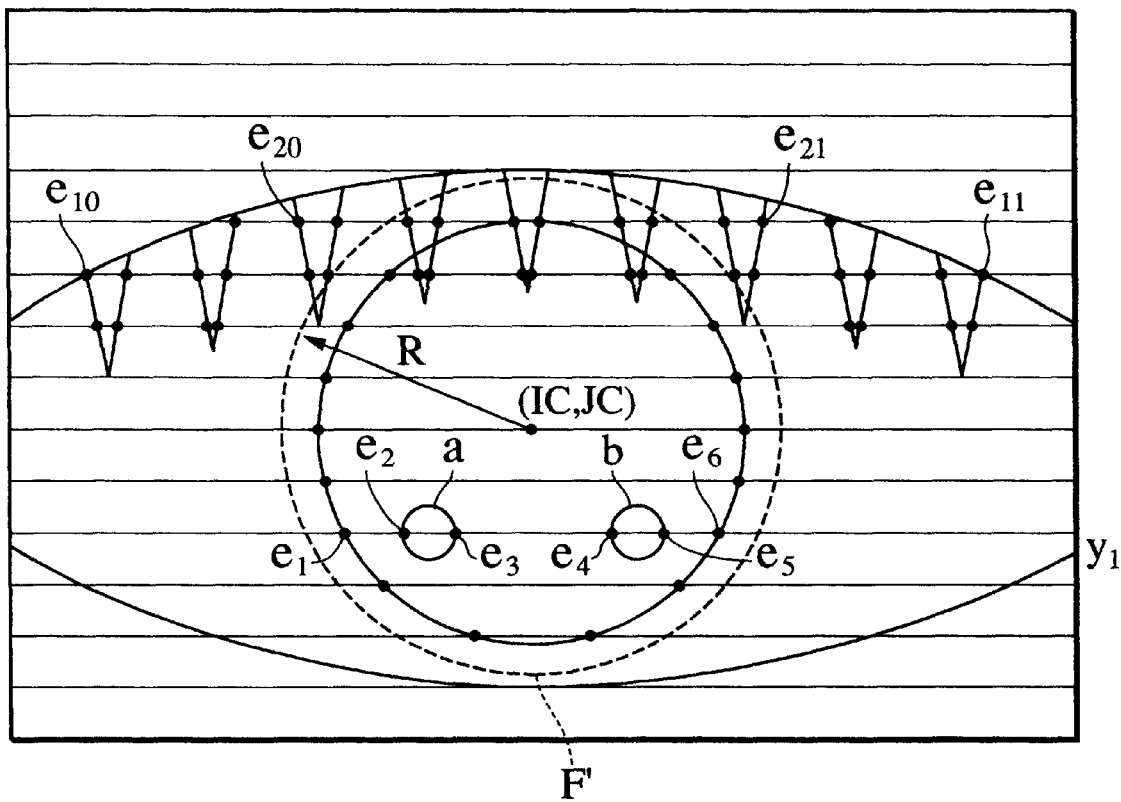
FIG. 7 is a view showing a pupil circle and a plurality of edges for supporting the operation in FIG. 6.
Figure 14:
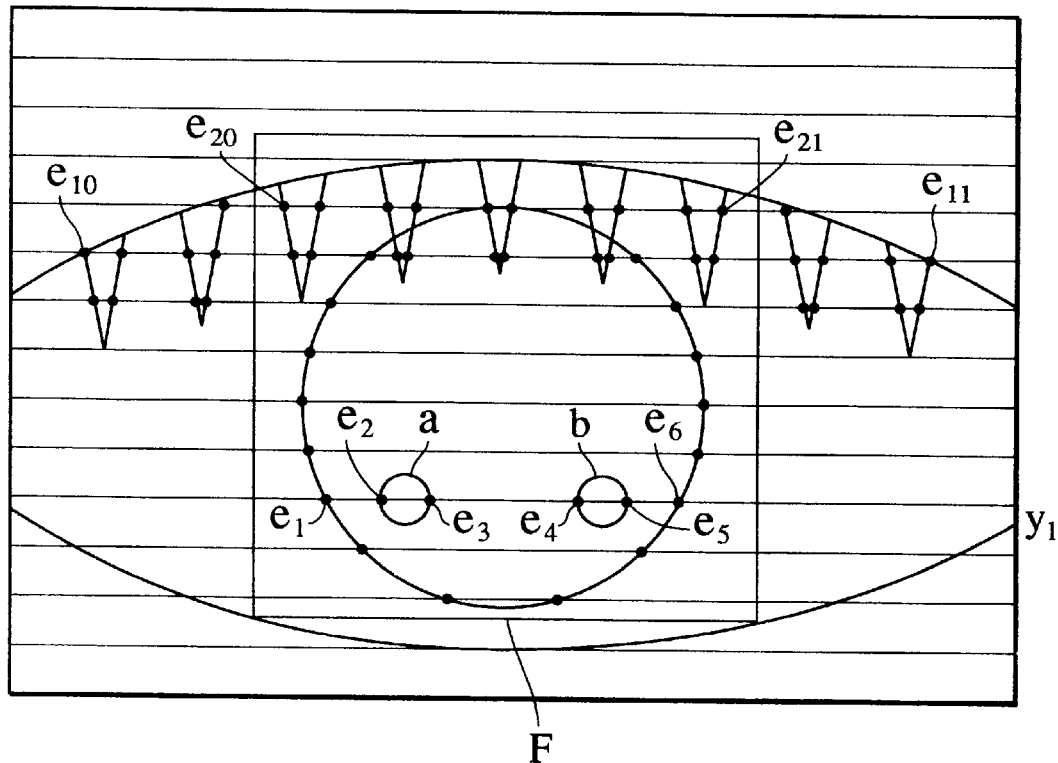
FIG. 14 is a view showing an eyeball image projected to the imaging device in FIG. 12.
Figure 15:
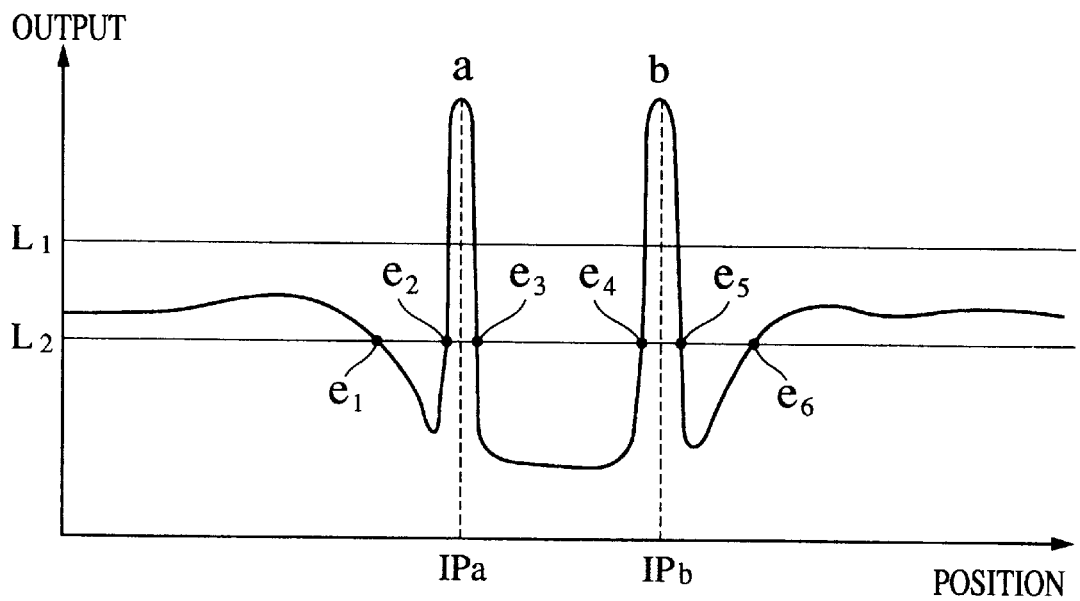
FIG. 15 is a graph explaining an output image of a line where Purkinje images exist on the imaging device and the extraction of pupil edges shown in FIG. 14.
Figure 16:
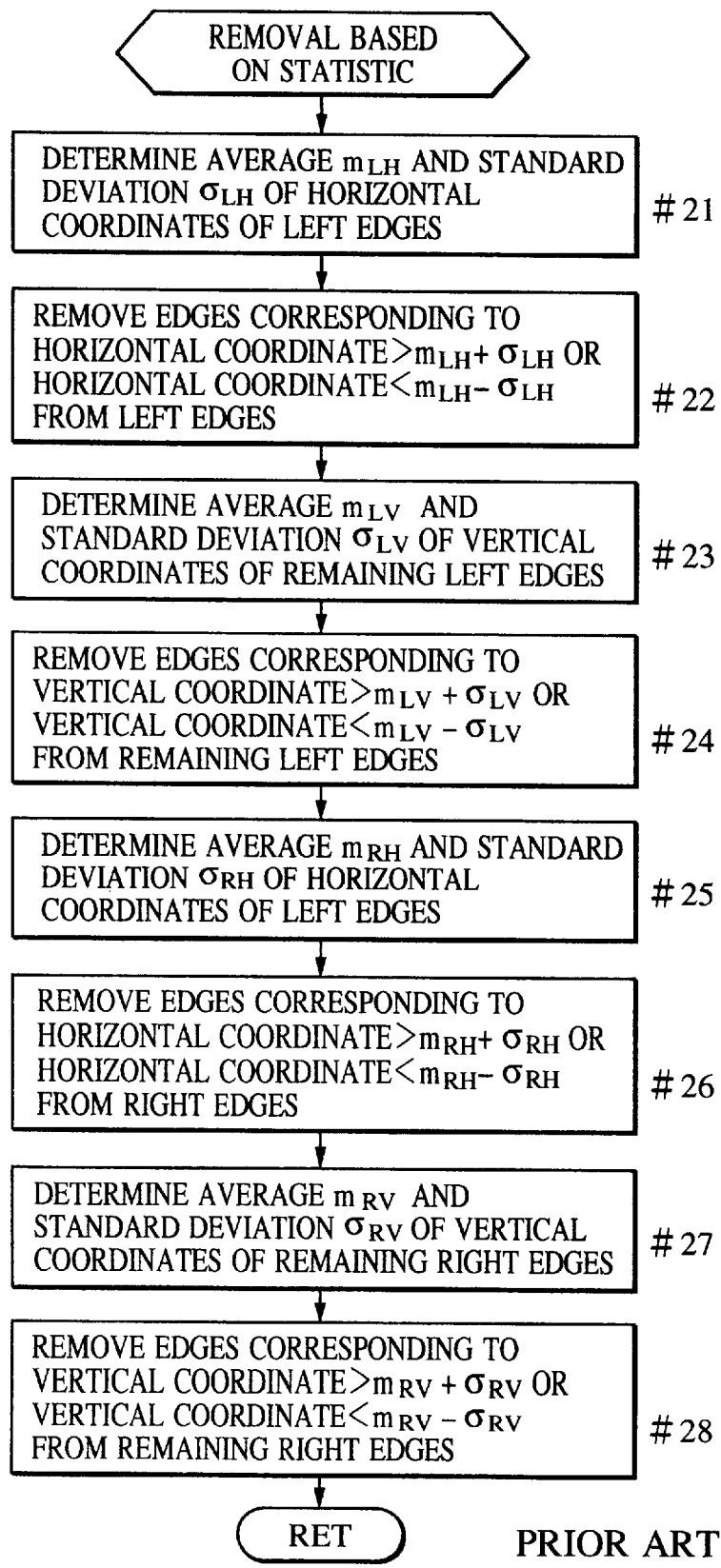
FIG. 16 is a flowchart showing a false pupil edge removing operation executed by a visual axis detecting device as a first conventional example.
Figure 17:
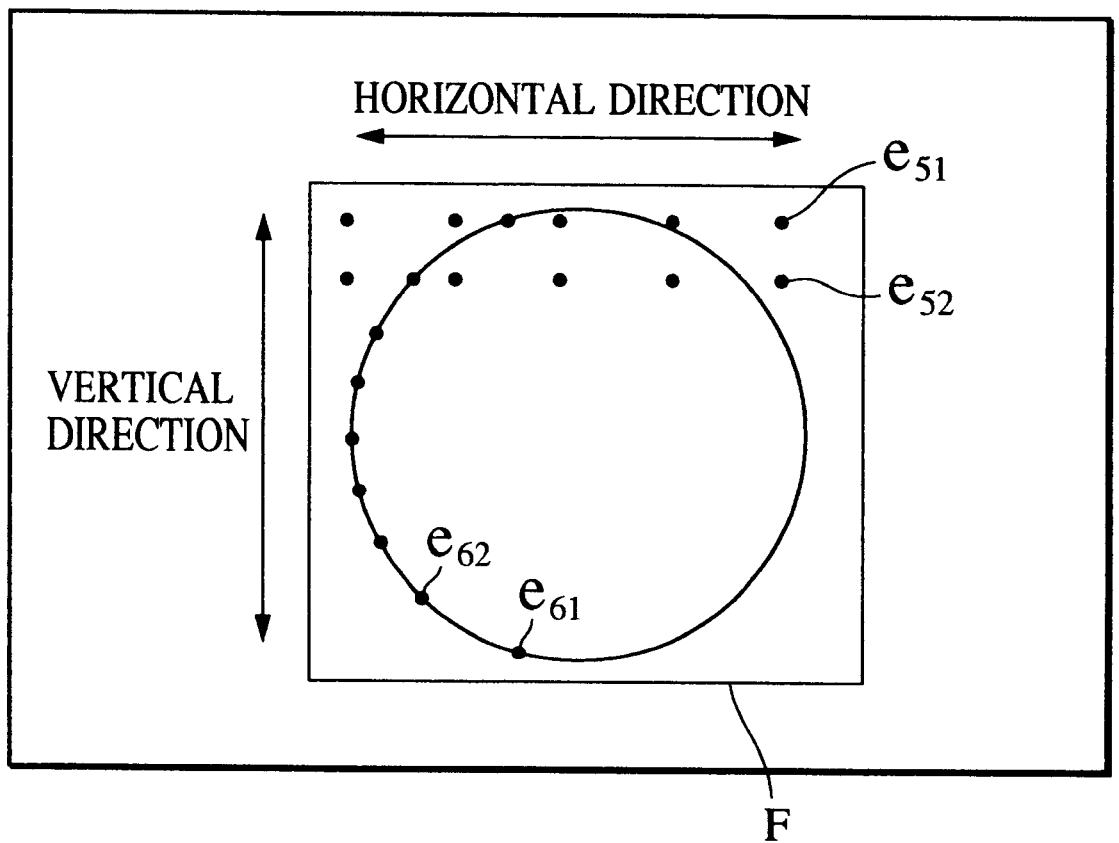
FIG. 17 is a view explaining the removal of edges in FIG. 16.
Figure 18:
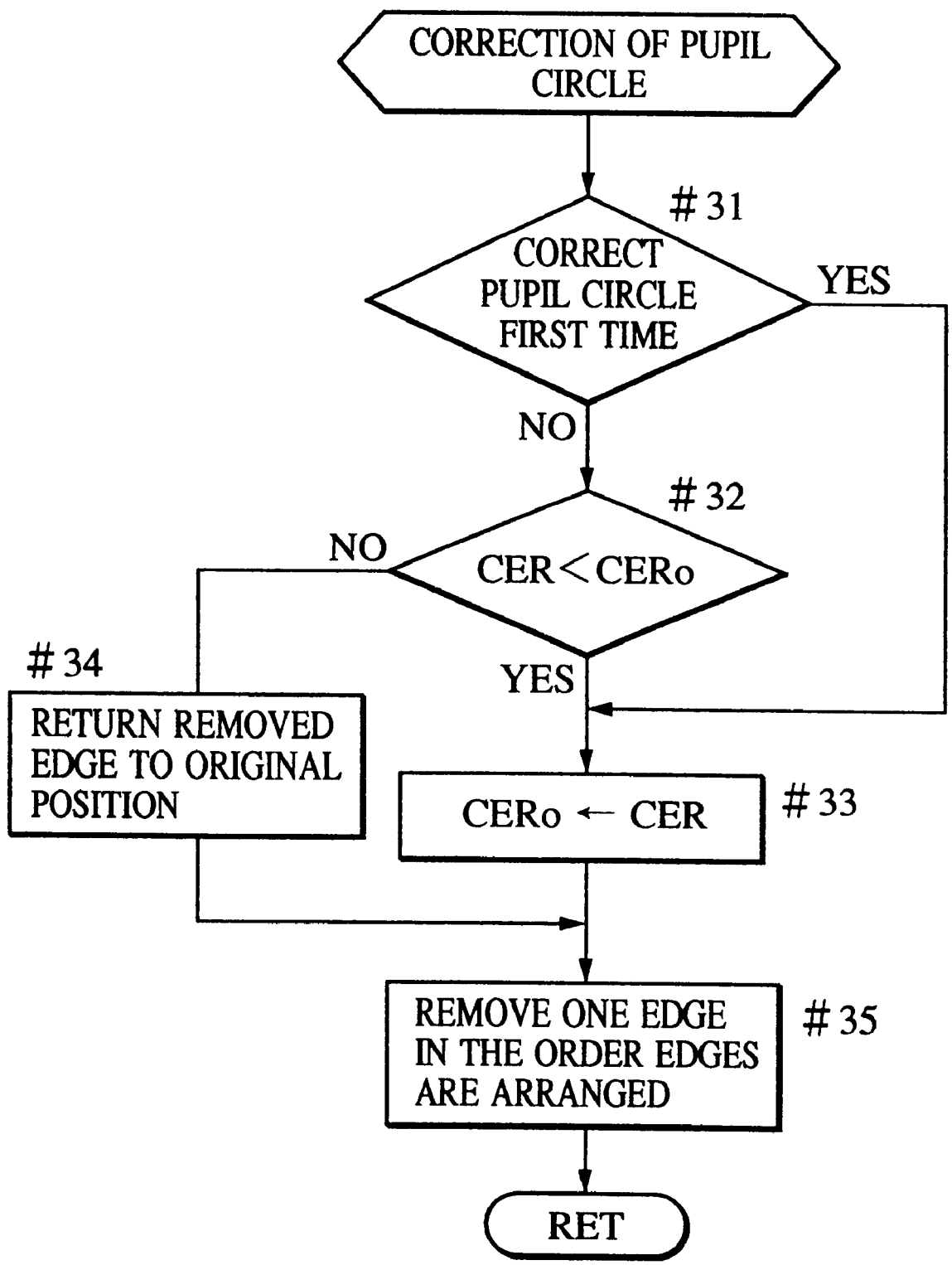
FIG. 18 is a flowchart showing a pupil circle correction operation executed based on a statistic by the visual axis detecting device as the first conventional example.

FIG. 7 is a view showing that the designated pupil range of the fourth embodiment is applied to an eyeball image similar to that shown in FIG. 14.

Figure 8:
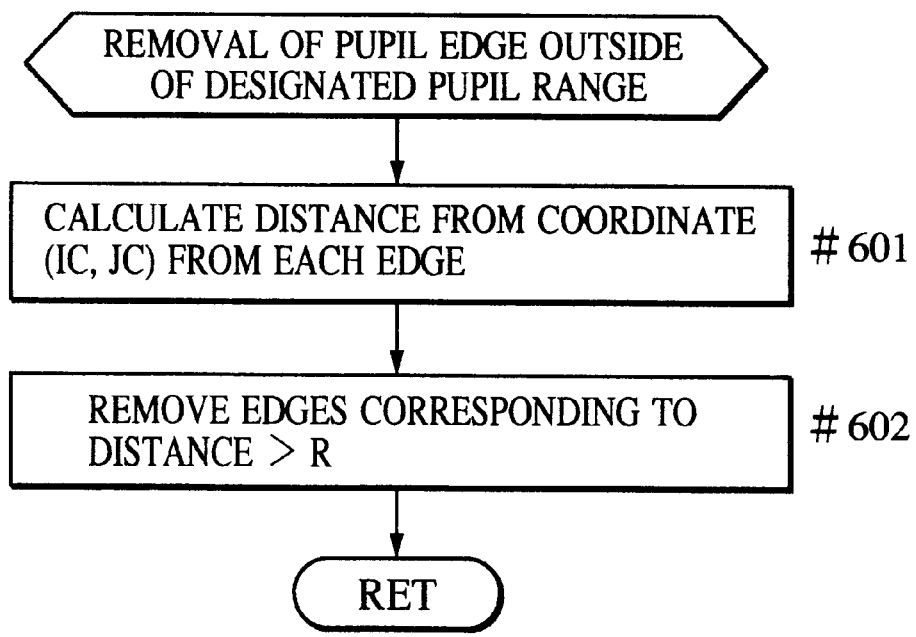
FIG. 8 is a flowchart showing a false pupil edge removing operation executed based on a statistic by the visual axis detecting device according to a fourth embodiment of this invention.
Figure 19:
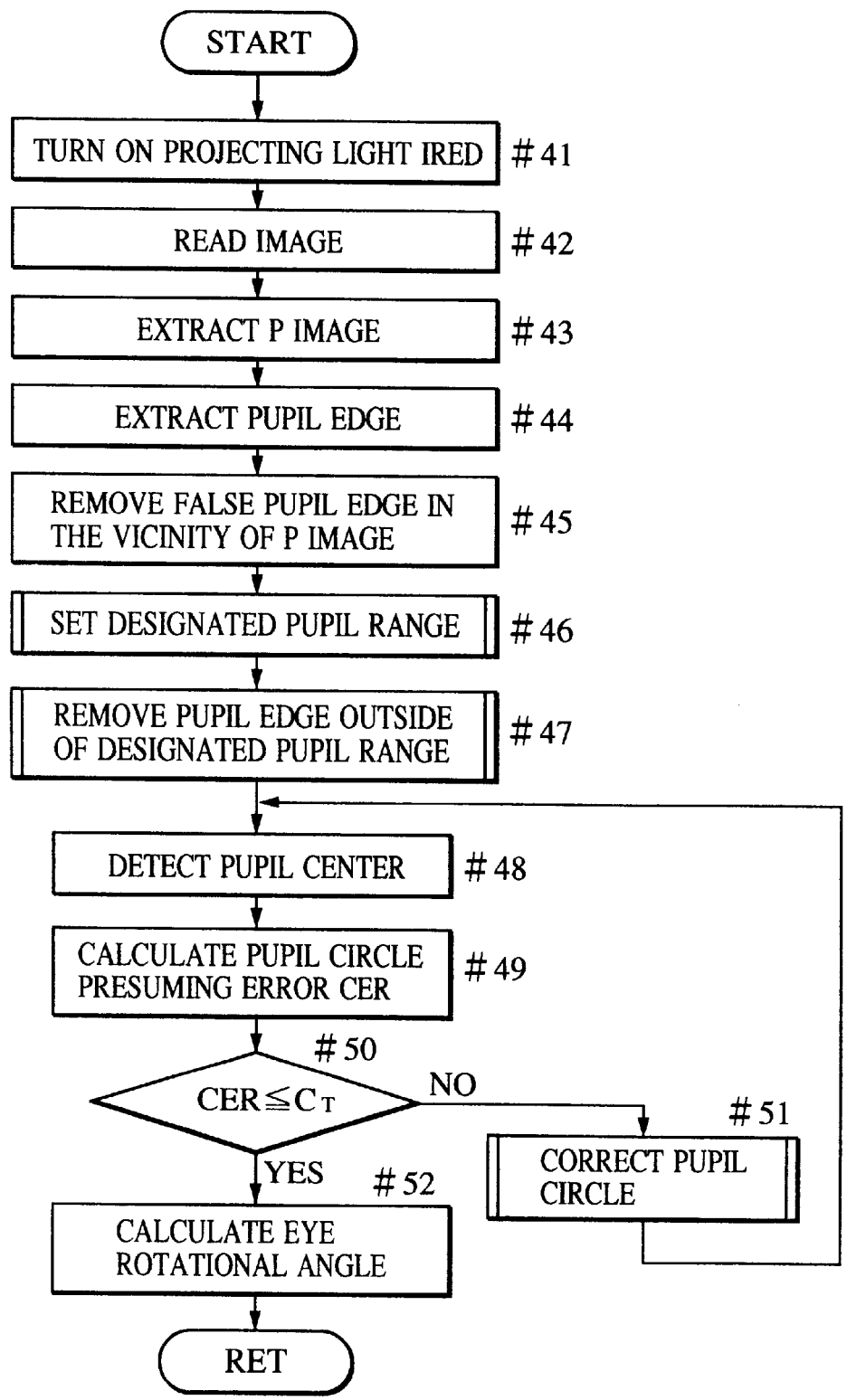
FIG. 19 is a flowchart showing the operation of the visual axis detecting device as a second conventional example.
Figure 20:
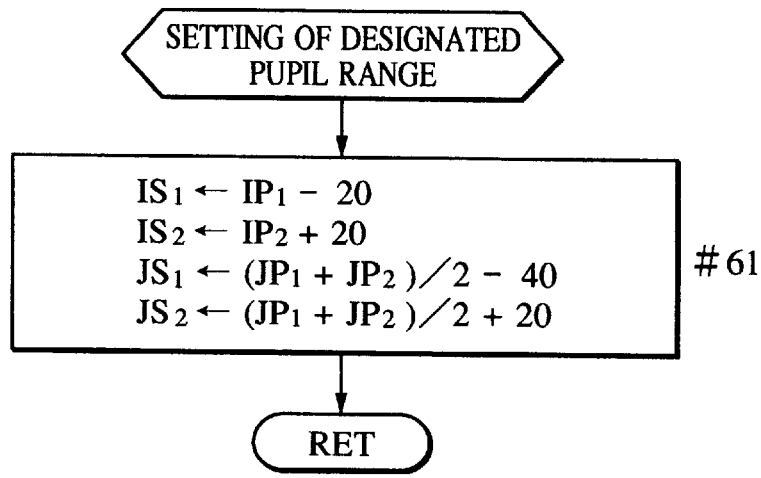
FIG. 20 is a flowchart showing a designated pupil range setting operation executed by the visual axis detecting device as the second conventional example.
Figure 21:
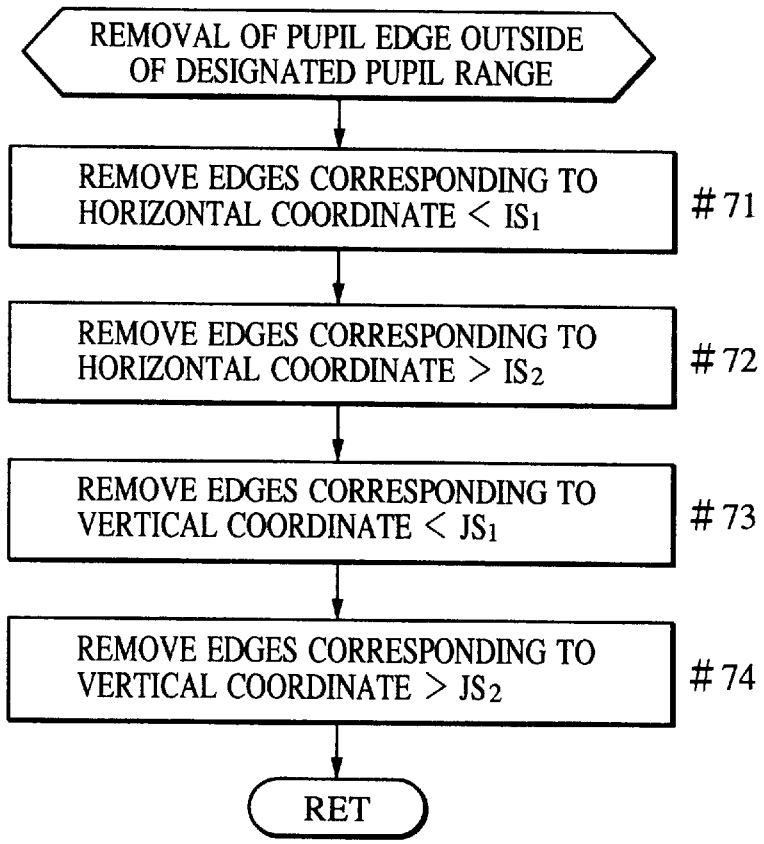
FIG. 21 is a flowchart showing a false pupil edge removing operation executed by the visual axis detecting device as the second conventional example.

FIG. 8 is a flowchart showing the operation of the "removal of the pupil edges outside of the designated pupil range" which is executed when the process goes to step #47 in FIG. 19.

In FIG. 8, a sequence controller 1 first calculates the distance of the coordinate (IC, JC) of a tentative pupil center position from each of the edges (step #601). For example, when a certain edge has a coordinate $(IE_1, JE_1)$, a distance $EC_1$ to be determined is represented by the following formula:

$$EC_1 = \sqrt{[(IC-IE_1)^2 + (JC-JE_1)^2]} \quad (3)$$

Edges which have a determined distance>R in comparison with the radius R of a designated pupil range are removed as false pupil edges (step #602) and the process returns to step #48 in FIG. 19.

Since this operation is effective to remove $e_{20}, e_{21}$ and the like shown in FIG. 7, the eight pieces in total of the false pupil edges can be additionally removed as compared with the conventional example shown in FIG. 14.

Figure 9:
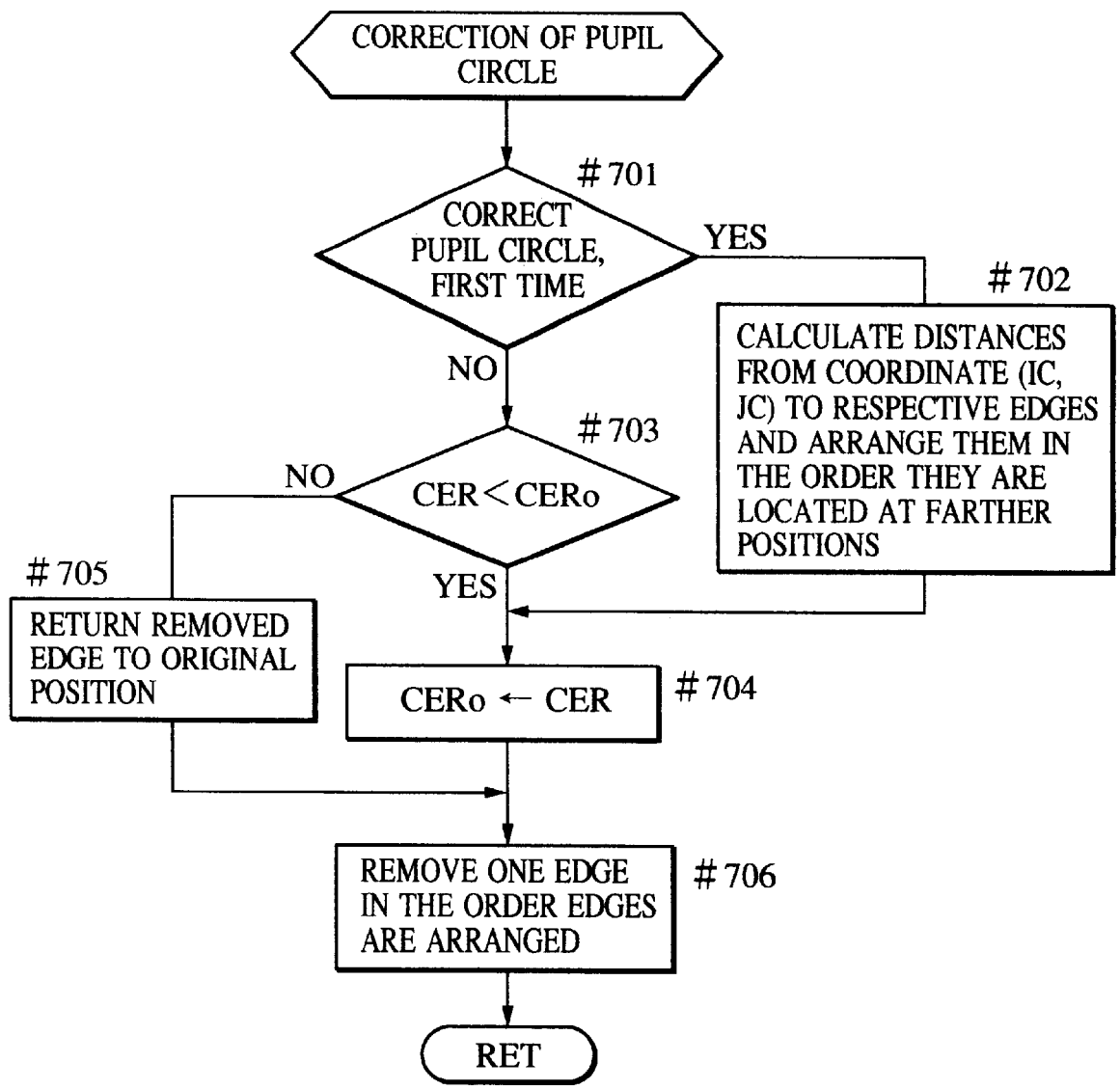
FIG. 9 is a flowchart showing a pupil circle correcting operation executed by the visual axis detecting device according to the fourth embodiment of this invention.

FIG. 9 is a flowchart showing the operation of the "correction of the pupil circle" which will be executed when the process goes to #51 in FIG. 19 in the fourth embodiment of this invention.

As is apparent from FIG. 3, almost all of the false pupil edges are caused by eyelashes, the ghost of spectacles, and the like and they are usually located outside of the pupil circle. Therefore, it may be contemplated that the edges which are located farther from the pupil center position have a higher possibility that they are the false pupil edges. When the edges which are located farther from the tentative pupil center position (which must be near to a true pupil center position) are removed in the order they are arranged making use of the above fact, the pupil circle can be effectively corrected, that is, the false pupil edges can be effectively removed.

In FIG. 9, the sequence controller 1 first checks whether the correction of the pupil circle is executed a first time (initial correction) or not (step #701). When it is corrected a first time, the distances of the coordinate (IC, JC) of a tentative pupil center position from each of the edges is calculated and the edges are rearranged in the order of the edges which have a longer distance (that is, in the order of the edges which are farther from the coordinate).

If the edges are divided into a plurality of edges such as the right edge group, the left edge group, and the like depending upon extracting conditions, the order of the edges may be rearranged in the respective groups.

Thereafter, a pupil circle estimating error CER is stored as $CER_0$ (step #704) and one edge is removed in the order edges are arranged (step #706). Since the edge is removed a first time here, the edge farthest from the coordinate (IC, JC) is removed.

When the correction of the pupil circle at step #701 is not the first time, that is, when the process returns to step #48 in FIG. 19 after the pupil circle is corrected the first time, the second time or thereafter and then executes the "correction of the pupil circle" again at step #51 because the pupil circle estimating error CER is not less than $C_T$ again at step #50, it is checked whether the thus determined latest pupil circle estimating error CER is made smaller than the pupil circle estimating error CER before the edge is removed, that is, smaller than $CER_0$ or not (step #703). Unless "CER<$CER_0$" here, the removed edge is returned to the original position because it is not a false pupil edge (step #705) and a next edge is removed in the order the edges are arranged (step #706).

When "CER<$CER_0$" at step #703, the removed edge is left as it is and the pupil circle estimating error CER is stored as $CER_0$ (step #704) and a next edge is removed in the order the edges are arranged (step #706).

Although the above embodiment shows an example that the radius R of the circle is set to 20 so that the region of the circle having the center located at the tentative pupil center position coincides with the designated pupil range, this invention is not limited thereto but, for example, the radius R may be set based on the average of the distances from the tentative pupil center position to the respective edges or the distribution of the distances.

According to the fourth embodiment, since the tentative pupil center position is estimated using the positions of the Purkinje images and the region of the circle determined by the distances therefrom is set as the designated pupil range for removing the false pupil edges, a larger number of false pupil edges can be more securely accurately removed as compared with the conventional apparatus.

Further, in the correction of the pupil circle, since it is assumed that the edges which are farther from the tentative pupil center position (which must be near to the position of the true pupil center) have a higher possibility that they are the false pupil edges and the edges are removed in the order they are located farther from that position, the correction of the pupil circle can be more effectively executed as compared with the conventional apparatus.

(Fifth Embodiment)

In the fourth embodiment, the edges are rearranged by calculating the distances from the coordinate (IC, JC) of the tentative pupil center position in the "correction of the circle" which is executed when the process goes to step #51 in FIG. 19. However, since the distances from the coordinate (IC, JC) have been calculated in the "removal of the pupil edges outside of the designated pupil range" at step #47, when the edges are rearranged in the subroutine, the time necessary to the calculation of the distances can be reduced to half only when the "correction of the pupil circle" is executed. This arangement will be described below as a fifth embodiment of this invention.

Figure 10:
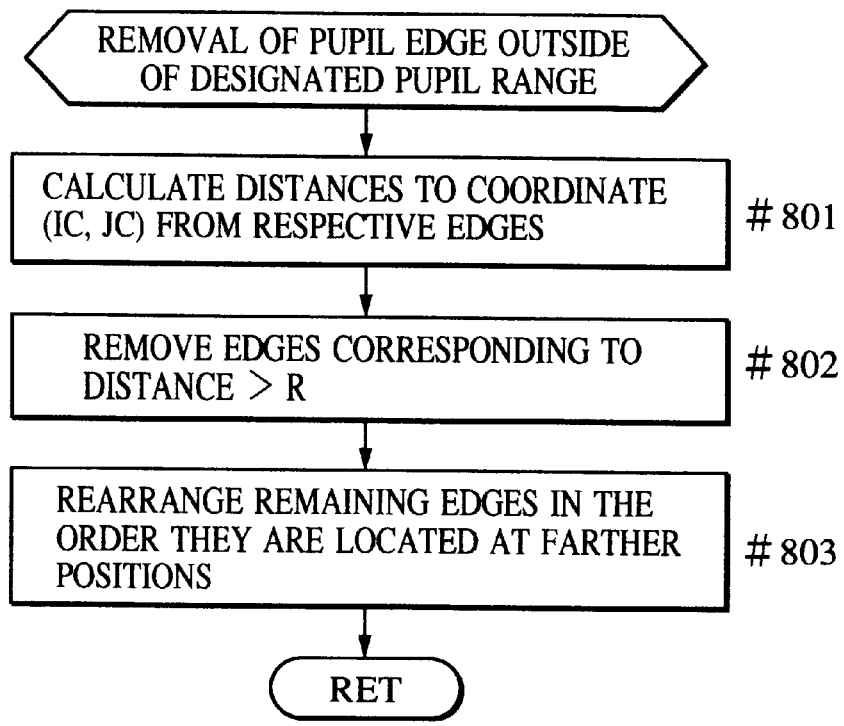
FIG. 10 is a flowchart showing a false pupil edge removing operation executed based on a statistic by the visual axis detecting device according to a fifth embodiment of this invention.

FIG. 10 is a flowchart showing the operation of the main portion of the visual axis detecting device according to the fifth embodiment of this invention. Since the electrical arrangement of the visual axis detecting device is the same as that shown in FIG. 12 and a series of operations of the visual axis detecting device is the same as that shown in FIG. 19 except for the processing of the "correction of the pupil circle" at step #51 in FIG. 19, the detailed description thereof is omitted here.

In FIG. 10, a sequence controller 1 first calculates the distances from respective edges to the coordinate (IC, JC) of a tentative pupil center position (step #801). The calculation is executed as in the first embodiment.

Edges which have a determined distance>R in comparison with the radius R of a designated pupil range are removed as false pupil edges (step #801). Then, the remaining edges which are not removed are rearranged in the order they are located farther away (step #803) and the process returns to step #48 in FIG. 19.

(Sixth Embodiment)

Although the fourth and fifth embodiments calculate the distances from the coordinate (IC, JC) by determining the root as shown in the formula (3), the calculation of the root takes time. Thus, when the comparison with the radius R and the like and the rearrangement of the edges are executed using the squares of the distances as they are without determining the root, a calculation time can be shortened as a whole as well as the same effect as that of the above embodiments can be obtained. This arrangement will be described below as a sixth embodiment.

Figure 11:
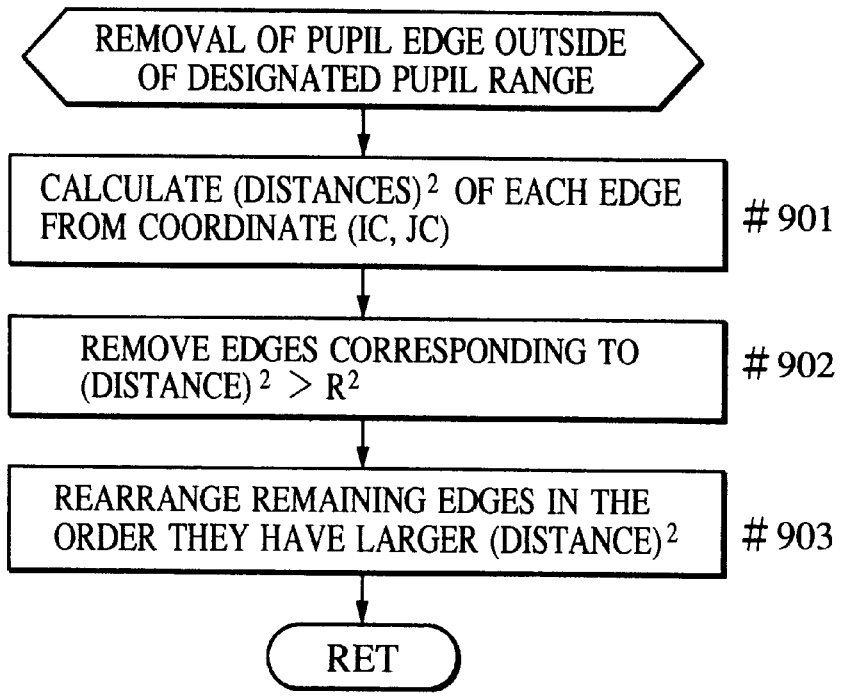
FIG. 11 is a flowchart showing a false pupil edge removing operation executed based on a statistic by the visual axis detecting device according to a sixth embodiment of this invention.

FIG. 11 is a flowchart showing the operation of the main portion of the visual axis detecting device according to the sixth embodiment of this invention. The electrical arrangement of the visual axis detecting device is the same as that shown in FIG. 12, the "setting of the designated pupil range" at step #45 in FIG. 19 is the same as that of the above fourth embodiment (FIG. 6) and the "removal of the pupil edges in a designated pupil range" at step #47 in FIG. 19 is as shown in FIG. 11 to be described below in a series of operations of the visual axis detecting device. Since the other operations are the same as those in FIG. 19, the detailed description thereof is omitted here.

In FIG. 11, a sequence controller 1 first calculates the square of the distances from respective edges to the coordinate (IC, JC) of a tentative pupil center position (step #901). The square $EC_1'$ of a distance to be determined is calculated from the following formula (4), where the coordinate of a certain edge is represented by ($IE_1$, $JE_1$).

$$EC_1'=(IC-IE_1)^2+(JC-JE_1)^2 \qquad (4)$$

The edges which correspond to (distance)$^2$>R2 are removed as false pupil edges using the determined squares of the distances of the respective edges and the radius R of the designated pupil range (step #902). Then, the remaining edges which are not removed are rearranged in the order they have a larger square of a distance (step #903) and the process returns to step #48 in FIG. 19.

According to the fourth to sixth embodiments, since the tentative pupil center position is estimated using the Purkinje image positions and the region of the circle (or the oval) determined by the distances therefrom is designated as the pupil range for removing false pupil edges, a larger number of the false pupil edges can be more accurately removed as compared with the conventional apparatus.

Further, in the estimated correction of the circle after the detection of the pupil center, since it is assumed that the edges which are farther from the tentative pupil center position have a higher possibility that they are the false pupil edges and the edges are removed in the order they are located farther, the correction of the pupil circle can be effectively executed as compared to the conventional apparatus.

(Seventh Embodiment)

Figure 22:
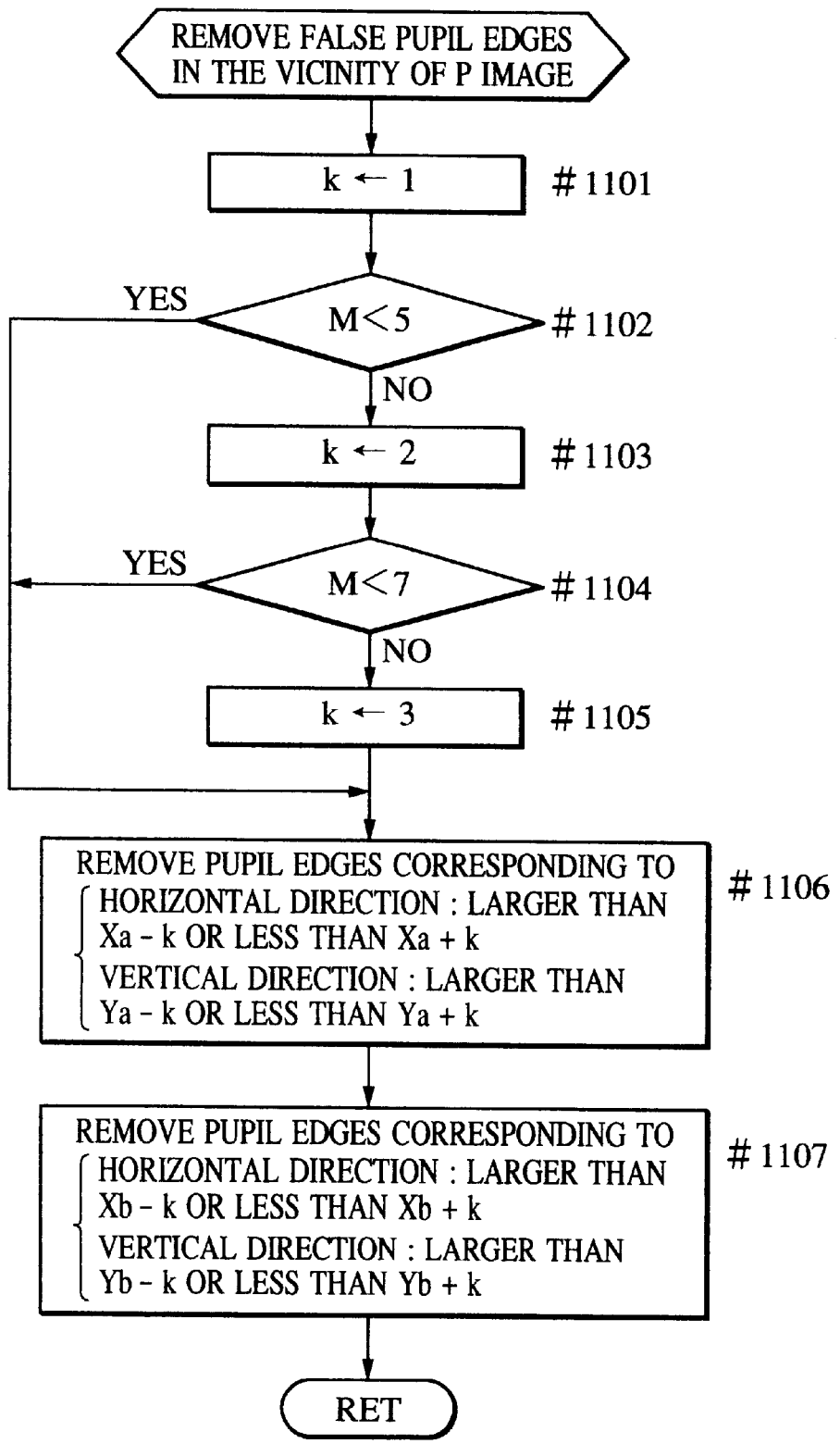
FIG. 22 is a flowchart showing the operation executed by the main portion of the visual axis detecting device according to a seventh embodiment of this invention.
Figure 24:
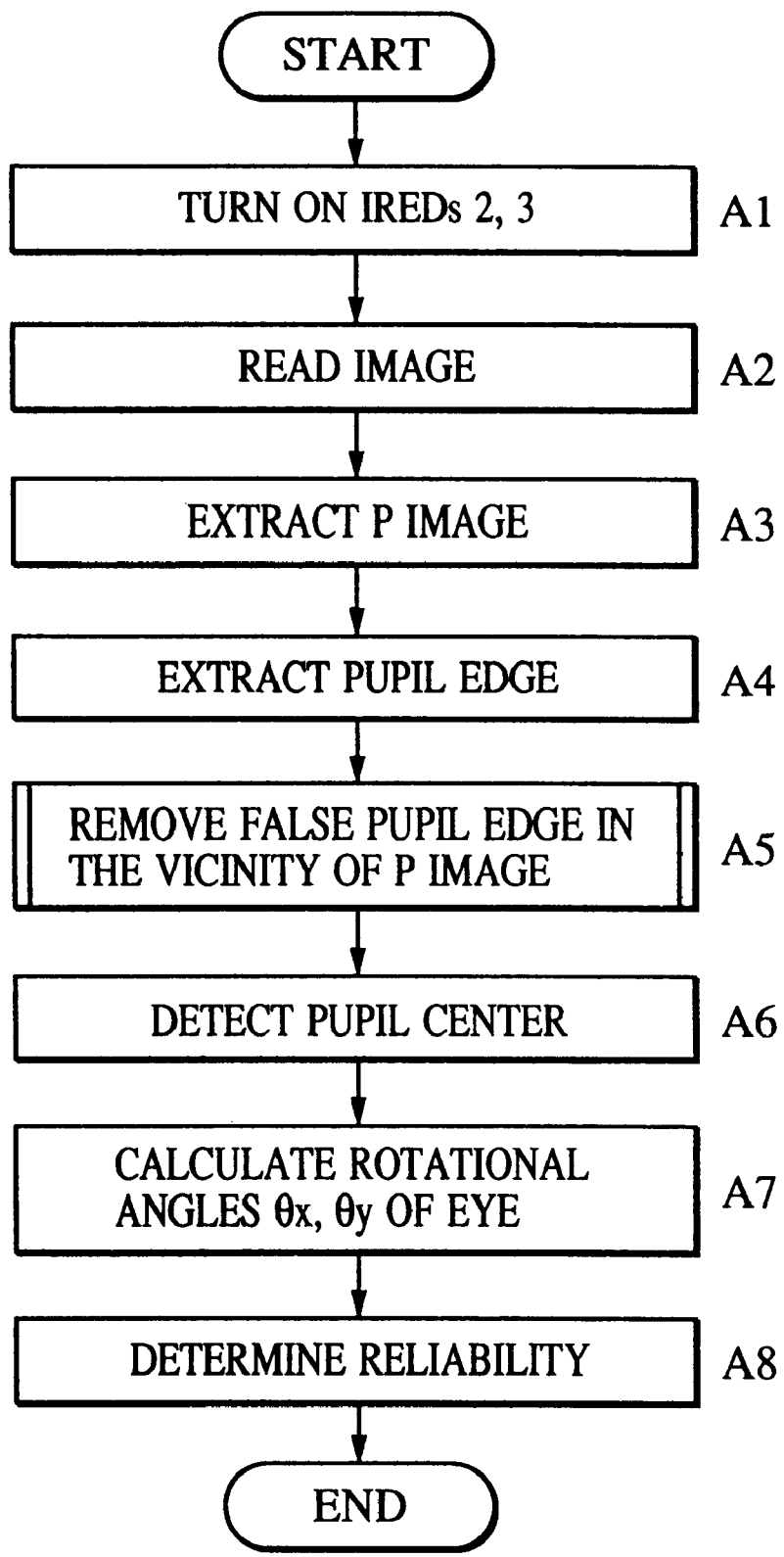
FIG. 24 is a flowchart showing a series of the operations executed by the visual axis detecting device as a third conventional example.
Figure 25:
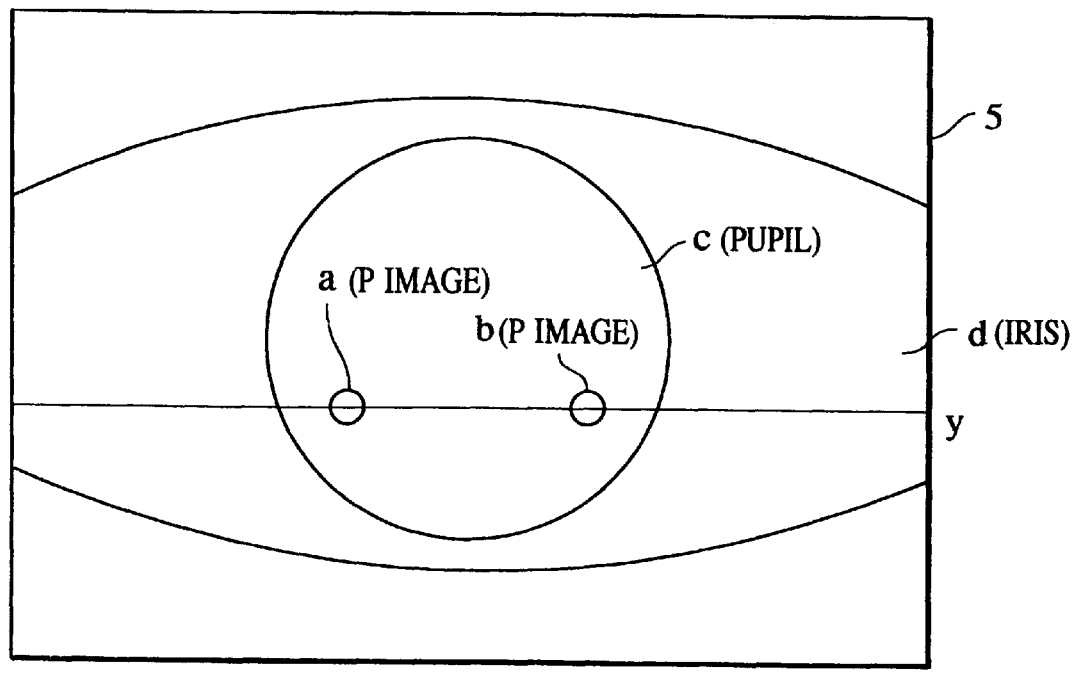
FIG. 25 is a view showing an eyeball image projected to the imaging device in FIG. 12.
Figure 26:
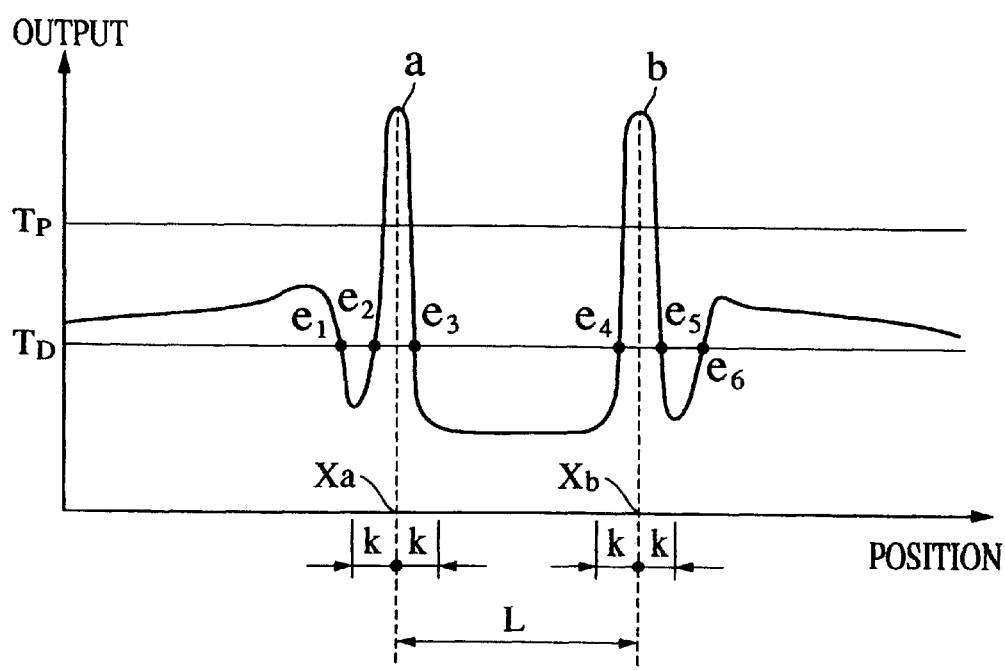
FIG. 26 a graph explaining an output image of a line where Purkinje images exist on the imaging device and the extraction of pupil edges shown in FIG. 25.

FIG. 22 is a flowchart showing the operation of the main portion of the visual axis detecting device according to a seventh embodiment of this invention. Since the electrical arrangement of the visual axis detecting device is the same as that shown in FIG. 12 and a series of operations of the visual axis detecting device is the same as that shown in FIG. 24 except the processing for removing the pupil edges in the vicinity of Purkinje images at step #5 in FIG. 24, the detailed description thereof is omitted here.

The processing for removing the pupil edges in the vicinity of Purkinje images in the visual axis detecting device will be described with reference to the flowchart shown in FIG. 22.

A sequence controller 1 first sets the width k of the region for removing the false pupil edges in the vicinity of the Purkinje images to 1 (step #1101). Next, the interval M between the two Purkinje images (which corresponds to the interval L shown in FIG. 5) is determined and it is checked whether it is less than 5 or not (step #1102). When it is less than 5, the process jumps to step #1106 while maintaining "k=1", whereas when it is equal to or grater than 5, "k=2" is set (step #1103) and then it is checked whether M is less than 7 or not (step #1104). As a result, when it is less than 7, the process jumps to step #1106 while maintaining "k=2", whereas when it is equal to or greater than 7, "k=3" is set (step #1105) and the process jumps to step #1106.

Figure 27:
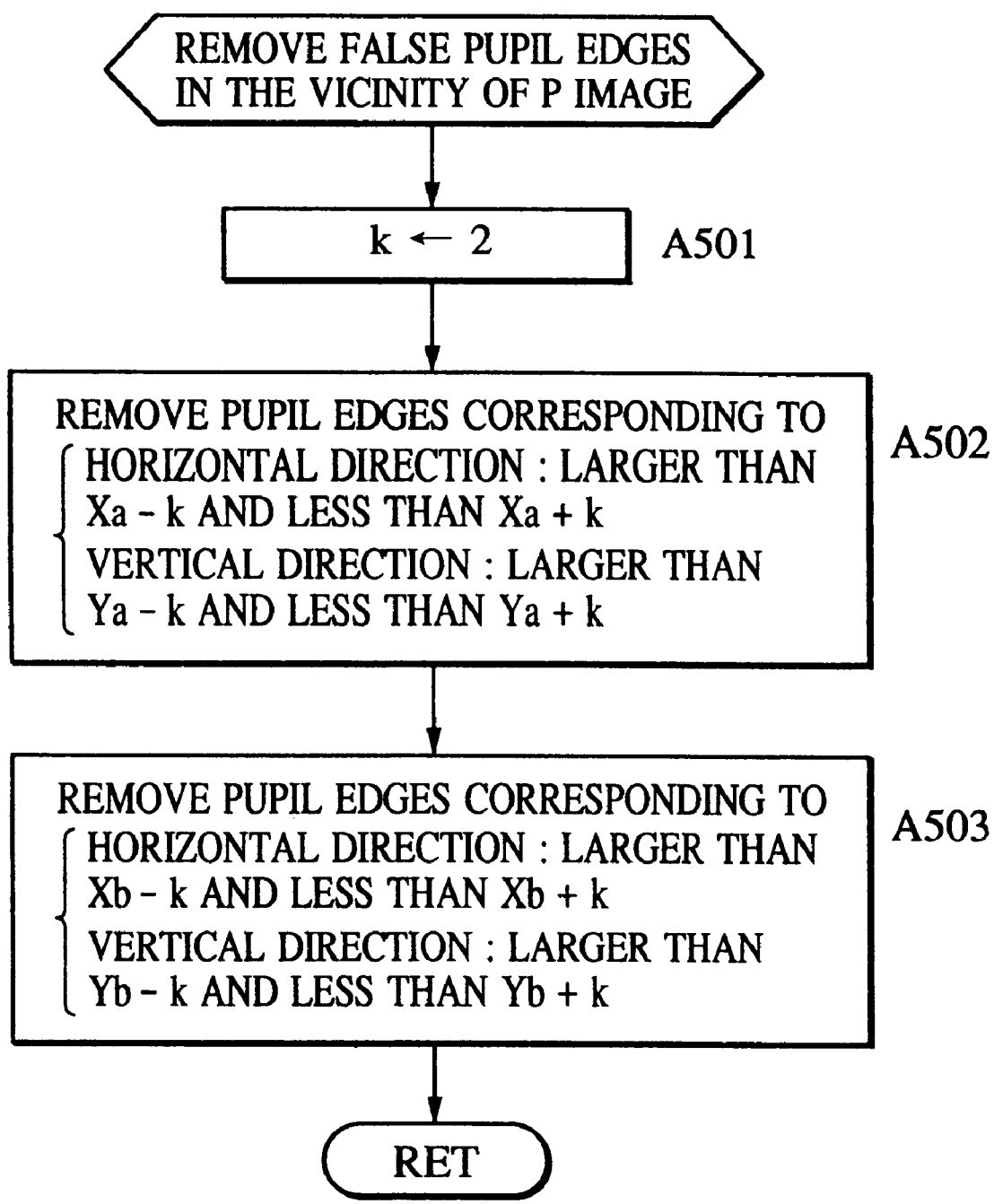
FIG. 27 is a flowchart showing the operation executed by the main portion of the visual axis detecting device as the third conventional example.
Figure 28:
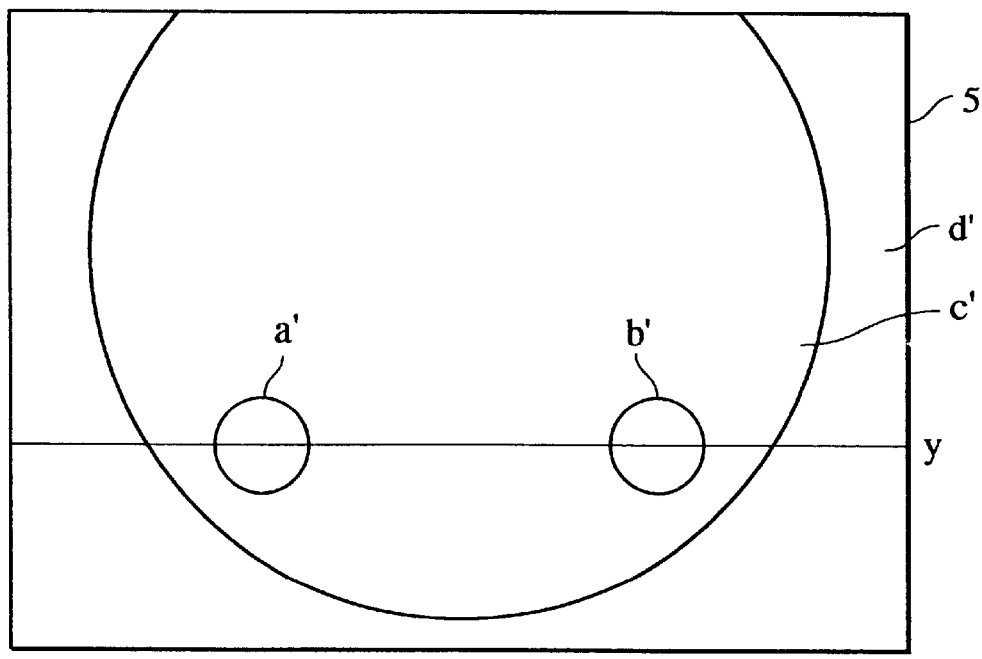
FIG. 28 is a view showing an example of an eyeball image on an imaging device when a correct pupil edge cannot be extracted by the visual axis detecting device as the third example.
Figure 29:
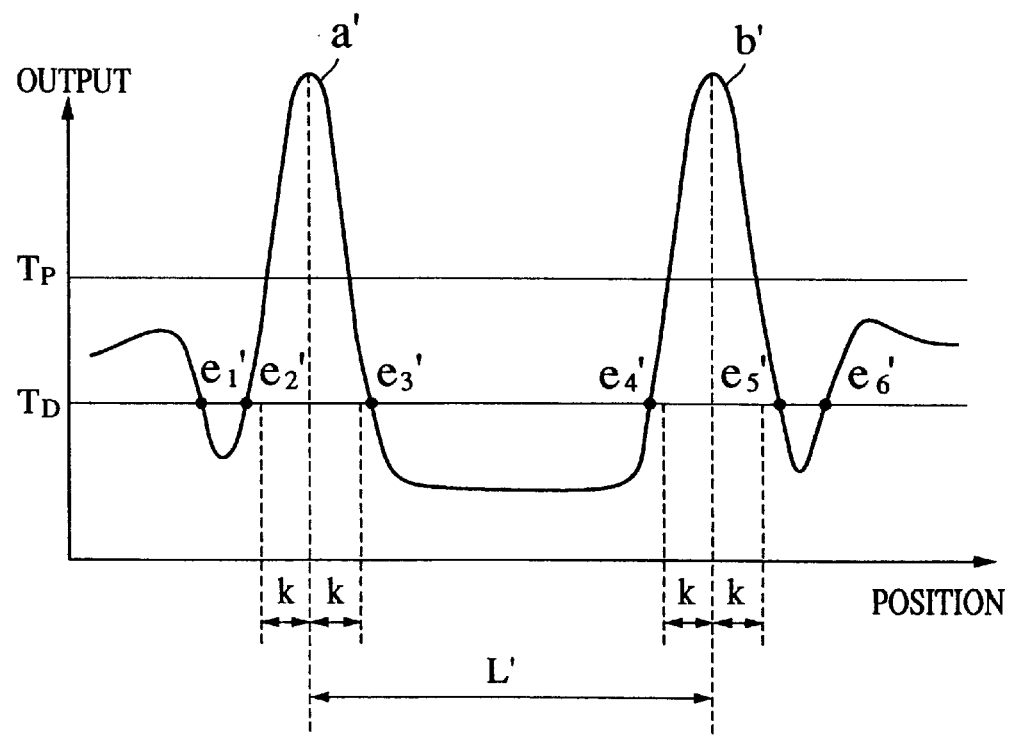
FIG. 29 is a graph explaining an output image of a line where Purkinje images exist on the imaging device and the extraction of a pupil edge shown in FIG. 28.

Next, the sequence controller 1 removes the edge portions in the respective ranges which are equal to or greater than (Xa−k) and equal to or less than (Xa+k) in a horizontal direction and equal to or greater than (Ya−k) and equal to or less than (Ya+k) in a vertical direction as the removal of the bottom portion of a Purkinje image a as in step #A502 in FIG. 27 (step #1106). Finally, the sequence controller 1 removes the edge portions in the respective ranges which are equal to or greater than (Xb−k) and equal to or less than (Xb+k) in the horizontal direction and equal to or greater than (Yb−k) and equal to or less than (Yb+k) in the vertical direction as the removal of the bottom portion of a Purkinje image b (step #1107) and the process moves to the processings at step #A6 and the steps subsequent to it as described above.

According to the seventh embodiment, the interval between the pair of Purkinje images is regarded as the size of the eyeball image and the Purkinje images on an imaging device 5 in the removal of the false pupil edges in the bottom portion of the Purkinje images and the width of the region for removing the false pupil edges in the vicinity of the Purkinje images are increased by assuming that when the interval between the pair of the Purkinje images is increased, the eyeball image and Purkinje images on the imaging device 5 are large and the region for removing the false pupil edges in the vicinity of the Purkinje images is decreased by assuming that when the interval between the pair of the Purkinje images is decreased, the eyeball image and Purkinje images on the imaging device 5 are small. As a result, the false pupil edges in the bottom portion of the Purkinje images can be properly removed regardless of the size of the eyeball image and Purkinje images on the imaging device 5, whereby a visual axis can be correctly detected.

(Eighth Embodiment)

Figure 23:
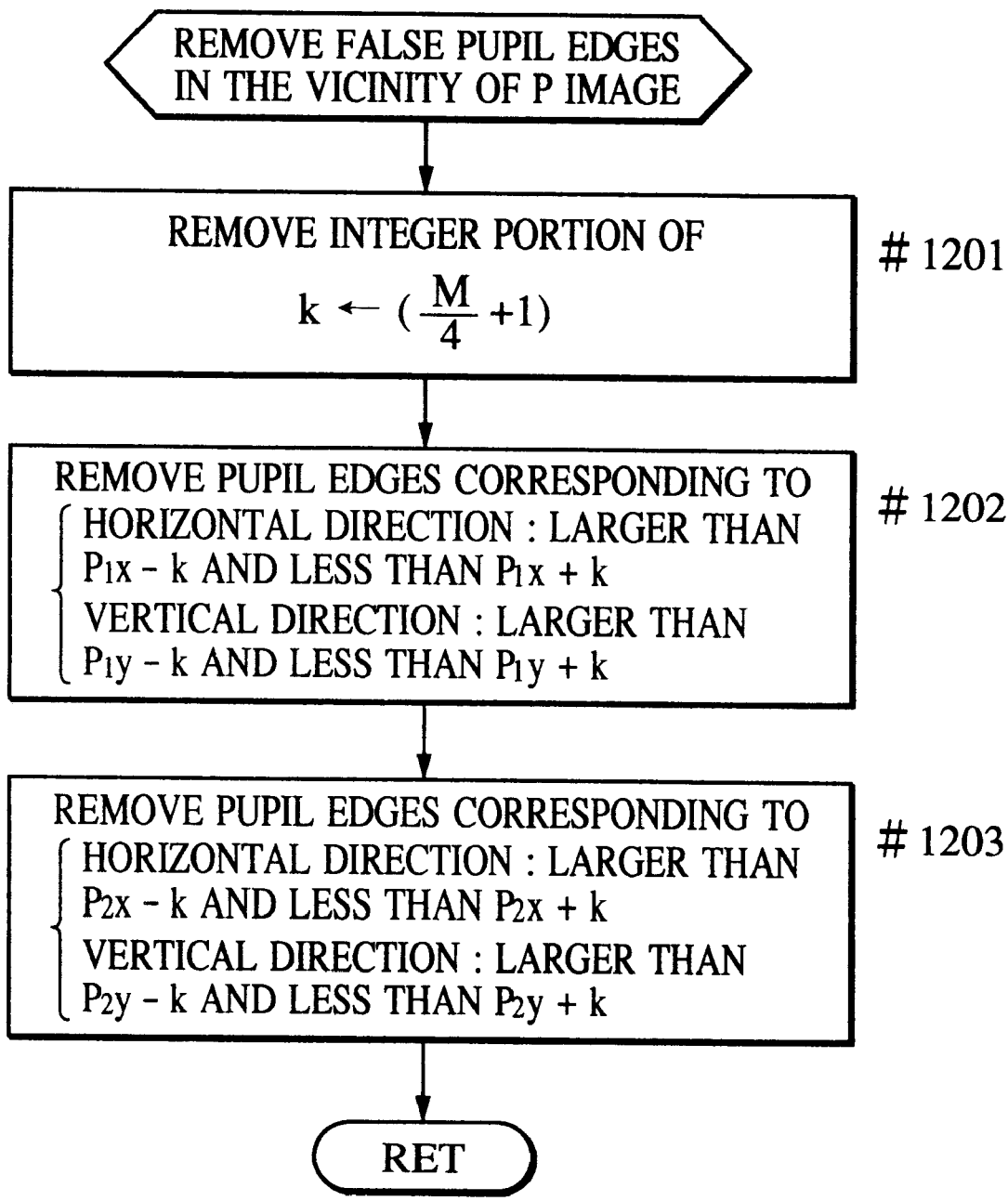
FIG. 23 is a flowchart showing the operation executed by the main portion of the visual axis detecting device according to an eighth embodiment of this invention.

FIG. 23 is a flowchart showing the operation of the main portion of the visual axis detecting device according to an eighth embodiment of this invention. Since the electrical arrangement of the visual axis detecting device is the same as that described in FIG. 12 and a series of operations of the visual axis detecting device is the same as that described in FIG. 24 except the processing for removing the pupil edges in the vicinity of Purkinje image at step #5 in FIG. 24, the detailed description thereof is omitted here.

Although the two threshold values are set to the interval M of the pair of the Purkinje images and the width k of the region for removing the false pupil edges in the vicinity of the Purkinje image is set in the seventh embodiment, they may be set by the relation between M (the interval of the Purkinje images) and k (the width of the region for removing the false pupil edges in the vicinity of the Purkinje image), which will be described below with reference to the flowchart shown in FIG. 23.

The sequence controller 1 first sets the relation between k and M as shown in the following formula (5) and determines k by substituting the value of M for the formula (5) (step #1201).

$$K = M/4 + 1 \quad (5)$$

For example, when "M=8", k is 3. Thereafter, the sequence controller 1 removes the edge portions in the respective ranges which are equal to or greater than (Xa−k) and equal to or less than (Xa+k) in a horizontal direction and equal to or greater than (Ya−k) and equal to or less than (Ya+k) in a vertical direction as the removal of the bottom portion of a Purkinje image a as in the seventh embodiment (step #1202). Finally, the sequence controller 1 removes the edge portions in the respective ranges which are equal to or greater than (Xb−k) and equal to or less than (Xb+k) in the horizontal direction and equal to or greater than (Yb−k) and equal to or less than (Yb+k) in the vertical direction as the removal of the bottom portion of a Purkinje image b (step #1203) and the process moves to step #A6 and the steps subsequent to it in FIG. 24 as described above.

Also, in the eighth embodiment, the interval between the pair of Purkinje images is regarded as the size of the eyeball image and the Purkinje images on an imaging device 5 in the removal of the false pupil edges in the bottom portion of the Purkinje images and the width of the region for removing the false pupil edges in the vicinity of the Purkinje images are increased by assuming that when the interval between the pair of the Purkinje images is increased, the eyeball image and Purkinje images on the imaging device 5 are large. Whereas, the region for removing the false pupil edges in the vicinity of the Purkinje images is decreased by assuming that when the interval between the pair of the Purkinje images is decreased, the eyeball image and Purkinje images on the imaging device 5 are small. As a result, the false pupil edges in the bottom portion of the Purkinje images can be properly removed regardless of the size of the eyeball image and Purkinje images on the imaging device 5, whereby a visual axis can be correctly detected.

Further, the arrangement of the eighth embodiment permits the false pupil edges to be more properly removed as compared with the seventh embodiment which sets the value k to "2" and "3".

(Modification)

According to the above respective embodiments, although the width of the region for removing the false pupil edges in the vicinity of the Purkinje images is changed based on the interval of the Purkinje images by regarding the interval between the Purkinje images as the size of the eyeball image and the Purkinje images on the imaging device, this invention is not limited thereto but the false pupil edges can be more properly removed by taking the brightness in the vicinity of the eyeball image into consideration. More specifically, when the vicinity of the eyeball image is brighter than a predetermined value, the width of the region is further increased.

Further, the same effect can be obtained by such an arrangement that the distance from an imaging device to an eyeball is divided into a plurality of zones and the widths k of the regions corresponding to the respective zones for removing the false pupil edges in the vicinity of the Purkinje images are prestored in an EEPROM, respectively, as well as from what zone a user detects a visual axis is permitted to be input from an external switch or the like and when a certain zone is set by an external input, the visual axis detecting device reads out the value k corresponding to the zone (distance) from the EEPROM and sets the region for removing the false pupil edges in the vicinity of the Purkinje images based on the value k.

That is, the false pupil edges in the bottom portions of the Purkinje images can be properly removed regardless of the size of an eyeball on an imaging device 5 and a visual axis can be correctly detected in such an arrangement that the distance between the position of the eyeball of the user and an eye contact portion is regarded as the size of an eyeball image on the imaging device and when the position of the eyeball is near to the eye contact portion (when a near zone is selected), it is regarded that the eyeball image on the imaging device is large and the width of the region for removing the false pupil edges is increased in the the vicinity of the Purkinje images, whereas when the position of the eyeball is far from the eye contact portion (when a far zone is selected), it is regarded that the eyeball image on the imaging device is small and the width of the region for removing the false pupil edges in the vicinity of the Purkinje images is decreased.

What is claimed is:

1. A visual axis detecting device comprising:

an image sensor for imaging an eyeball image, the eyeball image including a plurality of Purkinje images and a plurality of detected pupil edges, the plurality of detected pupil edges including actual pupil edges and false pupil edges;

Purkinje image detection means for determining a position of each of the plurality of Purkinje images in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means defines a reference point from the position of the plurality of Purkinje images, determines a distance from the reference point to each of the plurality of detected pupil edges, and extracts the actual pupil edges from the plurality of detected pupil edges by statistically processing the distances; and visual axis detecting means for detecting a visual axis based on the plurality of Purkinje images and the actual pupil edges.

2. A visual axis detecting device according to claim 1, wherein said actual pupil edge extraction means divides the plurality of detected pupil edges into groups depending upon the position of each of the plurality of detected pupil edges, and extracts the actual pupil edges from the plurality of detected pupil edges grouped together in each of the groups.

3. A visual axis detecting device according to claim 1, wherein said actual pupil edge extraction means determines a reliability of each of the actual pupil edges.

4. A visual axis detecting device according to claim 3, wherein when the reliability of each of the actual pupil edges is determined, said actual pupil edge extraction means determines the reliability in an order that the actual pupil edges have a longer distance to the reference point.

5. A visual axis detecting device comprising:

an image sensor for imaging an eyeball image, the eyeball image including a plurality of Purkinje images and a plurality of detected pupil edges, the plurality of detected pupil edges including actual pupil edges and false pupil edges;

Purkinje image detection means for determining a position of each of the plurality of Purkinje images in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means defines a reference point from the position of the plurality of Purkinje images, and extracts the actual pupil edges from the plurality of detected pupil edges by extracting a portion of the plurality of detected pupil edges positioned within a circular region determined using the reference point as a center of the circular region; and visual axis detecting means for detecting a visual axis based on the plurality of Purkinje images and the actual pupil edges.

6. A visual axis detecting device according to claim 5, wherein the circular region is defined by the reference point as the center thereof and a radius, the radius is determined from an average of distances from the reference point to each of the plurality of detected pupil edges and using the average and a standard deviation of the distances.

7. A visual axis detecting device according to claim 5, wherein the circular region is defined by the reference point used as the center thereof and a preset radius.

8. A visual axis detecting device according to claim 5, wherein said actual pupil edge extraction means determines a reliability of each of the actual pupil edges.

9. A visual axis detecting device according to claim 8, wherein when the reliability of each of the actual pupil edges is determined, said actual pupil edge extraction means determines the reliability in an order that the actual pupil edges have a longer distance to the reference point.

10. A visual axis detecting device comprising:

an image sensor for imaging an eyeball image, the eyeball image including a plurality of Purkinje images and a plurality of detected pupil edges, the plurality of detected pupil edges including actual pupil edges and false pupil edges;

Purkinje image detection means for determining a position of each of the plurality of Purkinje images in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means sets a predetermined region about an approximate position of each of the plurality of Purkinje images, removes a portion of the plurality of detected pupil edges positioned in the predetermined region, and changes a size of the predetermined region depending upon an interval between the plurality of Purkinje images; and visual axis detecting means for detecting a visual axis based on the plurality of Purkinje images and the actual pupil edges.

11. A visual axis detecting device according to claim 10, wherein when the interval between the plurality of Purkinje images is no less than a predetermined value, said actual pupil edge extraction means increases the size of the predetermined region, and when the interval between the plurality of Purkinje images is less than the predetermined value, said actual pupil edge extraction means decreases the size of the predetermined region.

12. A visual axis detecting device comprising:

an image sensor for imaging an eyeball image, the eyeball image including a plurality of Purkinje images and a plurality of detected pupil edges, the plurality of detected pupil edges including actual pupil edges and false pupil edges;

distance detecting means for determining a distance between an eyeball and said image sensor using the eyeball image imaged by said image sensor;

Purkinje image detection means for determining a position of each of the plurality of Purkinje images in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means removes a portion of the plurality of detected pupil edges located within a predetermined region about an approximate position of each of the plurality of Purkinje images, and changes a size of the predetermined region depending upon the distance detected by said distance detecting means; and visual axis detecting means for detecting a visual axis based on the plurality of Purkinje images and the actual pupil edges.

13. A visual axis detecting device according to claim 12, wherein when the-distance detected by said distance detecting means is no less than a predetermined value, said actual pupil edge extraction means increases the size of the predetermined region, and when the distance detected by said distance detecting means is less than the predetermined value, said actual pupil edge extraction means decreases the size of the predetermined region.

14. An apparatus including a visual axis detecting device comprising:

an image sensor for imaging an eyeball image, the eyeball image including a plurality of Purkinje images and a plurality of detected pupil edges, the plurality of detected pupil edges including actual pupil edges and false pupil edges;

Purkinje image detection means for determining a position of each of the plurality of Purkinje images in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means defines a reference point from the position of the plurality of Purkinje images, determines a distance from the reference point to each of the plurality of detected pupil edges, and extracts the actual pupil edges from the plurality of detected pupil edges by statistically processing the distances; and visual axis detecting means for detecting a visual axis based on the plurality of Purkinje images and the actual pupil edges.

15. An apparatus including a visual axis detecting device according to claim 14, wherein said actual pupil edge extraction means divides the plurality of detected pupil edges into groups depending upon the position of each of the plurality of detected pupil edges, and extracts the actual pupil edges from the plurality of detected pupil edges grouped together in each of the groups.

16. An apparatus including a visual axis detecting device according to claim 14, wherein said actual pupil edge extraction means determines a reliability of each of the actual pupil edges.

17. An apparatus including a visual axis detecting device according to claim 16, wherein when the reliability of each of the actual pupil edges is determined, said actual pupil edge extraction means determines the reliability in an order that the actual pupil edges have a longer distance to the reference point.

18. An apparatus including a visual axis detecting device comprising:

an image sensor for imaging an eyeball image, the eyeball image including a plurality of Purkinje images and a plurality of detected pupil edges, the plurality of detected pupil edges including actual pupil edges and false pupil edges;

Purkinje image detection means for determining a position of each of the plurality of Purkinje images in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means defines a reference point from the position of the plurality of Purkinje images, and extracts the actual pupil edges from the plurality of detected pupil edges by extracting a portion of the plurality of detected pupil edges positioned within a circular region determined using the reference point as a center of the circular region; and visual axis detecting means for detecting a visual axis based on the plurality of Purkinje images and the actual pupil edges.

19. An apparatus including a visual axis detecting device according to claim 18, wherein the circular region is defined by the reference point as the center thereof and a radius, the radius is determined from an average of distances from the reference point to each of the plurality of detected pupil edges and using the average and a standard deviation of the distances.

20. An apparatus including a visual axis detecting device according to claim 18, wherein the circular region is defined by the reference point used as the center thereof and a preset radius.

21. An apparatus including a visual axis detecting device according to claim 18, wherein said actual pupil edge extraction means determines a reliability of each of the actual pupil edges.

22. An apparatus including a visual axis detecting device according to claim 21, wherein when the reliability of each of the actual pupil edges is determined, said actual pupil edge extraction means determines the reliability in an order that the actual pupil edges have a longer distance to the reference point.

23. An apparatus including a visual axis detecting device comprising:

an image sensor for imaging an eyeball image, the eyeball image including a plurality of Purkinje images and a plurality of detected pupil edges, the plurality of detected pupil edges including actual pupil edges and false pupil edges;

Purkinje image detection means for determining a position of each of the plurality of Purkinje images in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means sets a predetermined region about an approximate position of each of the plurality of Purkinje images, removes a portion of the plurality of detected pupil edges positioned in the predetermined region, and changes a size of the predetermined region depending upon an interval between the plurality of Purkinje images; and visual axis detecting means for detecting a visual axis based on the plurality of Purkinje images and the actual pupil edges.

24. An apparatus including a visual axis detecting device according to claim 23, wherein when the interval between the plurality of Purkinje images is no less than a predetermined value, said actual pupil edge extraction means increases the size of the predetermined region, and when the interval between the plurality of Purkinje images is less than the predetermined value, said actual pupil edge extraction means decreases the size of the predetermined region.

25. An apparatus including a visual axis detecting device comprising:

an image sensor for imaging an eyeball image, the eyeball image including a plurality of Purkinje images and a plurality of detected pupil edges, the plurality of detected pupil edges including actual pupil edges and false pupil edges;

distance detecting means for determining a distance between an eyeball and said image sensor using the eyeball image imaged by said image sensor;

Purkinje image detection means for determining a position of each of the plurality of Purkinje images in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means removes a portion of the plurality of detected pupil edges located within a predetermined region about an approximate position of each of the plurality of Purkinje images, and changes a size of the predetermined region depending upon the distance detected by said distance detecting means; and visual axis detecting means for detecting a visual axis based on the plurality of Purkinje images and the actual pupil edges.

26. An apparatus including a visual axis detecting device according to claim 25, wherein when the distance detected by said distance detecting means is no less than a predetermined value, said actual pupil edge extraction means increases the size of the predetermined region, and when the distance detected by said distance detecting means is less than the predetermined value, said actual pupil edge extraction means decreases the size of the predetermined region.

27. A visual axis detecting device comprising:

an image sensor for imaging an eyeball image, the eyeball image including a Purkinje image and a plurality of detected pupil edges, the plurality of detected pupil edges including actual pupil edges and false pupil edges;

distance detecting means for determining a distance between an eyeball and said image sensor;

Purkinje image detecting means for determining a position of the Purkinje image in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means removes a portion of the plurality of detected pupil edges located within a region predetermined using the position of the Purkinje image, and changes a size of the region depending upon the distance detected by said distance detecting means; and visual axis detecting means for detecting a visual axis based on the Purkinje images and the actual pupil edges.

28. A visual axis detecting device according to claim 27, wherein when the distance detected by said distance detecting means is no less than a predetermined value, said actual pupil edge extraction means increases the size of the predetermined region, and when the distance detected by said distance detecting means is less than the predetermined value, said actual pupil edge extraction means decreases the size of the predetermined region.

29. An apparatus including a visual axis detecting device comprising:

an image sensor for imaging an eyeball image, the eyeball image including a Purkinje image and a plurality of detected pupil edges, the plurality of detected pupil edges including actual pupil edges and false pupil edges;

distance detecting means for determining a distance between an eyeball and said image sensor;

Purkinje image detection means for determining a position of the Purkinje image in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means removes a portion of the plurality of detected pupil edges located within a region predetermined using the position of the Purkinje image, and changes a size of the predetermined region depending upon the distance detected by said distance detecting means; and visual axis detecting means for detecting a visual axis based on the Purkinje image and the actual pupil edges.

30. An apparatus including a visual axis detecting device according to claim 29, wherein when the distance detected by said distance detecting means is no less than a predetermined value, said actual pupil edge extraction means increases the size of the predetermined region, and when the distance detected by said distance detecting means is less than the predetermined value, said actual pupil edge extraction means decreases the size of the predetermined region.

31. A visual axis detecting device comprising:

an image sensor for imaging an eyeball image, the eyeball image including a Purkinje image and a plurality of detected pupil edges, the plurality of detected pupil edges including actual pupil edges and false pupil edges;

Purkinje image detection menas for determining a position of the Purkinje image in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means defines a reference point from the position of the Purkinje image, and extracts the actual pupil edges from the plurality of detected pupil edges by extracting a portion of the plurality of detected pupil edges positioned within a circular region determined using the reference point as a center of the circular region; and visual axis detecting means for detecting a visual axis based on the Purkinje image and the actual pupil edges.

32. A visual axis detecting device according to claim 31, wherein the circular region is defined by the reference point as the center thereof and a radius, the radius is determined from an average of distances from the reference point to each of the plurality of detected pupil edges and using the average and a standard deviation of the distances.

33. A visual axis detecting device comprising:

an image sensor for imaging an eyeball image, the eyeball image including a Purkinje image and a plurality of detected pupil edges, the plurality of detected pupil edges including actual pupil edges and false pupil edges;

distance detecting means for determining a distance between an eyeball and said image sensor using the eyeball image imaged by said image sensor;

Purkinje image detection means for determining a position of the Purkinje image in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means removes a portion of the plurality of detected pupil edges located within a predetermined region about an approximate position of the Purkinje image, and changes a size of the predetermined region depending upon the distance detected by said distance detecting means; and visual axis detecting means for detecting a visual axis based on the Purkinje image and the actual pupil edges.

34. A visual axis detecting device according to claim 33, wherein when the distance detected by said distance detecting means is no less than a predetermined value, said actual pupil edge extraction means increases the size of the predetermined region, and when the distance detected by said distance detecting means is less than the predetermined value, said actual pupil edge extraction means decreases the size of the predetermined region.

35. An apparatus including a visual axis detecting device comprising;

an image sensor for imaging an eyeball image, the eyeball image including a Purkinje image and a plurality of detected pupil edges, the plurality of detected pupil edges including actual pupil edges and false pupil edges;

Purkinje image detection means for determining a position of the Purkinje image in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means defines a reference point from the position of the Purkinje image, and extracts the actual pupil edges from the plurality of detected pupil edges by extracting a portion of the plurality of detected pupil edges positioned within a circular region determined using the reference point as a center of the circular region; and visual axis detecting means for detecting a visual axis based on the Purkinje image and the actual pupil edges.

36. An apparatus including a visual axis detecting device according to claim 35, wherein the circular region is defined by the reference point as the center thereof and a radius, the radius is determined from an average of distances from the reference point to each of the plurality of detected pupil edges and using the average and a standard deviation of the distances.

37. An apparatus including a visual axis detecting device comprising:

an image sensor for imaging an eyeball image, the eyeball image including a Purkinje image and a plurality of detected pupil edges, the plurality of detected pupil edges including actual pupil edges and false pupil edges;

distance detecting means for determining a distance between an eyeball and said image sensor using the eyeball image imaged by said image sensor;

Purkinje image detection means for determining a position of the Purkinje image in the eyeball image;

detected pupil edge detection means for determining a position of each of the plurality of detected pupil edges in the eyeball image;

actual pupil edge extraction means for extracting actual pupil edges from the plurality of detected pupil edges in the eyeball image, wherein said actual pupil edge extraction means removes a portion of the plurality of detected pupil edges located within a predetermined region about an approximate position of the Purkinje image, and changes a size of the predetermined region depending upon the distance detected by said distance detecting means; and visual axis detecting means for detecting a visual axis based on the plurality of Purkinje images and the actual pupil edges.

38. An apparatus including a visual axis detecting device according to claim 37, wherein when the distance detected by said distance detecting means is no less than a predetermined value, said actual pupil edge extraction means increases the size of the predetermined region, and when the distance detected by said distance detecting means is less than the predetermined value, said actual pupil edge extraction means decreases the size of the predetermined region.

* * * * *

UNITED STATES PATENT AND TRADEMARK OFFICE
CERTIFICATE OF CORRECTION

PATENT NO.   :  6,036,316
DATED        :  March 14, 2000
INVENTOR(S)  :  Hiroshi ARITA It is certified that error appears in the above-identified patent and that said Letters Patent is hereby corrected as shown below:

COLUMN 1:

Line 67, "positions of them" should read --their positions-- .

COLUMN 3:

Line 26, "#29):" should read --#28):--.

COLUMN 11:

Line 65, "(distance to $C_O)^2 < m_{LF2} - \sigma_{LF2}$" should read --(distance to $C_O)^2 < m_{LF2} - \sigma_{LF2}$.--.

COLUMN 12:

Line 5, "(distance to $C_O)^2 < m_{RF2} - \sigma_{RF2}$" should read --(distance to $C_O)^2 < m_{RF2} - \sigma_{RF2}$.--.
Line 41, "distance to $C_O > m_F - \sigma_F$." should read --distance to $C_O > m_F + \sigma_F$ or--.
Line 42, "distance to $C_O < m_F - \sigma_F$" should read --distance to $C_O < m_F - \sigma_F$.--.
Line 47, "imagges," should read --images,--.

COLUMN 14:

Line 58, "securely" should be deleted.

UNITED STATES PATENT AND TRADEMARK OFFICE
CERTIFICATE OF CORRECTION

PATENT NO.   : 6,036,316
DATED        : March 14, 2000
INVENTOR(S)  : Hiroshi ARITA It is certified that error appears in the above-identified patent and that said Letters Patent is hereby corrected as shown below:

<u>COLUMN 16</u>:

Line 16, "farther," should read --farther away,--.

<u>COLUMN 20</u>:

Line 61, "the-distance" should read --the distance--.

Signed and Sealed this

Eighth Day of May, 2001

*Attest:*

NICHOLAS P. GODICI

*Attesting Officer*   Acting Director of the United States Patent and Trademark Office